United States Patent [19]
Wallace et al.

[11] Patent Number: 5,814,307
[45] Date of Patent: Sep. 29, 1998

[54] METHOD FOR REGULATING CELL GROWTH, LEUKOCYTE DIFFERENTIATION AND TUMOR CELL GROWTH USING ONCOSTATIN M TO STIMULATE SYNTHESIS OF IL-6

[75] Inventors: Philip M. Wallace, Seattle; Thomas J. Brown, Poulsbo, both of Wash.

[73] Assignee: Bristol-Myers Squibb Company, New York, N.Y.

[21] Appl. No.: 312,205

[22] Filed: Sep. 26, 1994

Related U.S. Application Data

[63] Continuation-in-part of Ser. No. 129,230, Sep. 29, 1993, abandoned, which is a continuation-in-part of Ser. No. 504,486, Apr. 4, 1990, abandoned, which is a continuation-in-part of Ser. No. 335,399, Apr. 10, 1989, Pat. No. 5,202,116.

[51] Int. Cl.$^6$ .............................. A61K 38/18; C07K 14/54
[52] U.S. Cl. .................... 424/85.1; 424/85.2; 424/185.1; 514/12; 514/21; 530/351; 530/395
[58] Field of Search .......................... 424/85.1, 88, 85.2, 424/450, 489, 185.1; 514/12, 21; 530/351, 402, 403, 827, 395

[56] References Cited

U.S. PATENT DOCUMENTS 5,202,116  4/1993  Brown et al. ........................... 424/85.1

FOREIGN PATENT DOCUMENTS

| 290948 | 11/1988 | European Pat. Off. ........ C12N 15/00 |
| WO 90/12585 | 11/1990 | WIPO .............................. A61K 37/00 |
| WO 94/04190 | 3/1994 | WIPO .............................. A61K 45/05 |
| WO 94/05318 | 3/1994 | WIPO .............................. A61K 37/02 |

OTHER PUBLICATIONS

Bazan et al., 1991, Neuropoietic Cytokines In The Hematopoietic Fold, Neuron 7: 197–208.

Brown et al., 1987, Purification And Characterization Of Cytostatic Lymphyokines Produced By Activated Human T Lymphocytes, J. Immunol. 139 (No. 9): 2977–2983.

Brown et al., 1988, Oncostatin M Differentially Regulates The Action of Type I Transforming Growth Factor–β (TGF–β1), J. Cell. Biochem. Suppl. O (12 Part A): 194.

Brown et al., 1989, Oncostatin M As A Unique Modulator Of Endothelial Cell Surface Properties, J. Cell. Biochem. O (13 Part E): 189.

Brown et al., 1990, Molecular Biology Of The Cardiovascular System, UCLA Symposia On Molecular And Cellular Biology, Roberts et al. (eds.), Alan R. Liss, New York, pp. 195–206.

Brown et al., 1991, Regulation of IL–6 Expression By Oncostatin M, J. Immunol. 147: 2175–2180.

Chen et al., 1988, Growth Inhibition of Human Breast Carcinoma and Leukemia/Lymphoma Cell Lines By Recombinant Interferon–$β_2$, Proc. Natl. Acad. Sci. USA 85: 8037–8041.

Garman et al., 1987, B–Cell–Stimulatory Factor 2($β_2$ Interferon) Functions As A Second Signal For Interleukin 2 Production By Mature Murine T Cells, Proc. Natl. Acad. Sci. USA 84: 7629–7633.

Gearing et al., 1992, The IL–6 Signal Transducer, gp130: An Oncostatin M Receptor And Affinity Converter For The LIF Receptor, Science 255: 1434–1437.

Gordon et al., 1992, Growth Factors Affecting Human Thrombocytopoiesis: Potential Agents For The Treatment Of Thrombocytopenia, Blood 80: 302–307.

Grove et al., 1991 (a), Oncostatin M Up–Regulates Low Density Lipoprotein Receptors in HepG2 Cells By A Novel Mechanism, J. Biol. Chem. 266: 18194–18199.

Grove et al., 1991 (b), Macrophage–Derived Factors Increases Low Density Lipoprotein Uptake And Receptor Number In Cultured Human Liver Cells, J. Lipid Res. 32: 1889–1897.

Hamilton et al., 1991, Oncostatin M Stimulates Urokinase–type Plasminogen Activator Activity in Human Synovial Fibroblasts, Biochem. Biophys. Res. Comm. 180: 652–659.

Horn et al., 1990, Regulation of Cell Growth by Recombinant Oncostatin M, Growth Factors 2: 157–165.

Jirk et al., 1989, Bacterial Lipopolysaccharide And Inflammatory Mediators Augment IL–6 Secretion By Human Endothelial Cells, J. Immunol. 142 (No. 1): 144–147.

Kallestad et al., 1991, Disulfide Bond Assignment and Identification of Regions Required for Functional Activity of Oncostatin M, J. Biol. Chem. 266 (No. 14): 8940–8945.

Linsley et al., 1989, Identification And Characterization Of Cellular Receptors For The Growth Regulator, Oncostatin M, J. Biol. Chem. 264 (No. 8): 4282–4289.

Liu et al., 1992 (a), Regulation Of EGR–1, c–jun, And c–myc Gene Expression By Oncostatin M, Cell Growth And Diff. 3: 307–313.

Liu et al., 1992 (b), Interleukin–6 Signal Transducer gp130 Mediates Oncostatin M Signaling, J. Biol. Chem. 267: 16763–16766.

Malik et al., 1989, Molecular Cloning, Sequences Analysis, And Functional Expression Of A Novel Growth Regulator, Oncostatin M, Mol. Cell. Biol. 9 (No. 7): 2847–2853.

(List continued on next page.)

*Primary Examiner*—Thomas M. Cunningham
*Attorney, Agent, or Firm*—Pennie & Edmonds LLP

[57] ABSTRACT

The present invention relates to methods of using oncostatin M (OM). In particular, it relates to the use of OM to stimulate interleukin 6 (IL-6) synthesis in target cells, especially human endothelial cells. The resultant IL-6, in turn, may perform a variety of functions such as cell growth regulation, leukocyte differentiation, and tumor inhibition. Furthermore, the present invention also relates to the use of OM to treat cytopenias, including anemia and thrombocytopoiesis, and to increase tolerance to irradiation and cytotoxic drugs. Therefore, the methods of the invention may have a wide range of applications, including, but not limited to, the inhibition of tumor growth, the treatment of cytopenias, and to increase the tolerance to radio- and chemotherapy. OM may be used in combination with various cytokines, including erythropoietin, colony-stimulating factors, interleukin-3 or thrombopoietin.

4 Claims, 16 Drawing Sheets

OTHER PUBLICATIONS

May et al., 1989, Interleukin–6 Gene Expression In Human Endothelial Cells: RNA Start Sites, Multiuple IL–6 Proteins And Inhibition Of Proliferation, Biochem. Biophys. Res. Comm. 159 (No. 3): 991–998.

Miles et al., 1992, Oncostatin M As A Potent Mitogen For AIDS—Kaposi's Sarcoma–Derived Cells, Science 255: 1432–1434.

Mule et al., 1990, Antitumor Activity Of Recombinant Interleukin 6 In Mice, J. Exp. Med. 171: 629–636.

Nair et al., 1992, Identification Of A Major Growth Factor For AIDS—Kaposi's Sarcoma Cells As Oncostatin M, Science 255: 1430–1432.

Nishimoto et al., 1994, Oncostatin M, Leukemia Inhibitory Factor, And Interleukin 6 Induce The Proliferation Of Human Plasmacytoma Cells Via The Common Signal Transducer, J. Exp. Med. 179: 1343–1347.

Paul et al., 1990, Molecular Cloning Of A cDNA Encoding Interleukine 11, A Stromal Cell–Derived Lymphopoietic And Hematopoietic Cytokine, Proc. Natl. Acad. Sci. USA 87: 7512–7516.

Richards et al., 1992, Recombinant Oncostatin M Stimulates The Production Of Acute Phase Proteins In HepG2 Cells And Rat Primary Hepatocytes In Vitro, J. Immunol. 148: 1731–1736.

Richards et al., 1993, Selective Regulation Of Metalloproteinase Inhibitor (TIMP–1) by Oncostatin M In Fibroblasts In Culture, J. Immunol. 150 (No. 12): 5596–5603.

Rao et al., 1992, Oncostatin M Regulates VIP Expression In A Human Neuroblastoma Cell Line, Neuro Report 3: 865–868.

Rose et al., 1991, Oncostatin M Is A Member Of A Cytokine Family That Includes Leukemia–Inhibitory Factor, Granulocyte Colony–Stimulating Factor, And Interleukin 6, Proc. Natl. Acad. Sci. USA 88: 8641–8645.

Sehgal et al., 1987, Human $\beta_2$ Interferon and B–Cell Differentiation Factor BSF–2 Are Identical, Science 235: 731–732.

Taga et al., 1992, Functional Inhibition Of Hematopoietic And Neurotrophic Cytokines By Blocking The Interleukin 6 Signal Transducer gp130, Proc. Natl. Acad. Sci. USA 89: 10998–11001.

Takai et al., 1988, B Cell Stimulatory Factor–2 Is Involved In The Differentiation Of Cytotoxic T Lymphocytes, J. Immunol. 140 (No. 2): 508–512.

Yin et al., 1993, Involvement Of IL–6 Signal Transducer gp130 In IL–11–Mediated Signal Transduction, J. Immunol. 151: 2555–2561.

Zarling et al., 1986, Oncostatin M: A Growth Regulator Produced by Differentiated Histiocytic Lymphoma Cells, Proc. Natl. Acad. Sci. USA 83: 9739–9743.

W. F. Paul(ed.), Fundamental Immunology, 3rd edition, pp. 788–789. Raven Press, New York, 1993.

METHOD FOR REGULATING CELL GROWTH, LEUKOCYTE DIFFERENTIATION AND TUMOR CELL GROWTH USING ONCOSTATIN M TO STIMULATE SYNTHESIS OF IL-6

The present application is a continuation-in-part of U.S. patent application Ser. No. 08/129,230, filed Sep. 29, 1993, now abandoned, ; which is a continuation-in-part of U.S. patent application Ser. No. 07/504,486, filed Apr. 4, 1990 (now abandoned); which is a continuation-in-part of U.S. patent application Ser. No. 07/335,399, filed Apr. 10, 1989 (U.S. Pat. No. 5,202,116) each of which is incorporated by reference herein in its entirety.

1. INTRODUCTION

The present invention relates to methods of using oncostatin M (OM). In particular, it relates to the use of OM to stimulate interleukin 6 (IL-6) synthesis in target cells, especially human endothelial cells. The resultant IL-6, in turn, may perform a variety of functions such as cell growth regulation, leukocyte differentiation, and tumor inhibition. Furthermore, the present invention relates to the use of OM to induce thrombocytopoiesis and regulate other hematopoietic cell lineages. Therefore, the methods of the invention may have a wide range of applications, including, but not limited to, the inhibition of tumor growth, the induction of hematopoiesis and thrombocytopoiesis, and the promotion of wound healing.

2. BACKGROUND OF THE INVENTION

2.1. PROPERTIES OF ONCOSTATIN M

OM is a cytokine of 28,000 dalton molecular weight originally defined by its ability to inhibit growth of certain tumor cell lines but not normal fibroblasts (Zarling et al., 1986, *Proc. Natl. Acad. Sci. USA* 83:9739). It is a 196 amino acid glycoprotein that is first synthesized as a 252 amino acid precursor encoded by a ~2-kilobase transcript (Malik et al., 1989, *Mol. Cell. Biol.* 9:2847; Kallestad et al., 1991, *J. Biol. Chem.* 266:8940). OM is produced by monocytes, macrophages and activated T cells (Zarling et al., 1986, *Proc. Natl. Acad. Sci. USA* 83:9739; Brown et al., 1989, *J. Immunol.* 139:2977; Grove et al., 1991, *J. Lipid Res.* 32:1889). It belongs to a cytokine family whose members include IL-6, leukemia inhibitory factor (LIF), granulocyte colony stimulating factor (G-CSF), ciliary neurotrophic factor (CNTF), and myelomonocytic growth factor (MGF) (Bazan, 1991, *Neuron* 7:197; Rose and Bruce, 1991, *Proc. Natl. Acad. Sci. USA* 88:8641; Paul et al., 1990, *Proc. Natl. Acad. Sci. USA* 87:7512).

OM acts on a wide variety of targets cells and elicits a multitude of biological responses such as growth modulation (Zarling et al., 1986, *Proc. Natl. Acad. Sci. USA* 83:9739; Horn et al., 1990, *Growth Factors* 2:157; Miles et al., 1992, *Science* 255:1432; Nair et al., 1992, *Science* 255:1430), leukemia cell differentiation (Rose and Bruce, 1991, *Proc. Natl. Acad. Sci. USA* 88:8641; Liu et al., 1992, *Cell Growth and Diff.* 3:307), low density lipoprotein receptor upregulation (Grove et al., 1991, *J. Biol. Chem.* 266:18194), stimulation of plasminogen activator (Brown et al., 1990, *Molecular Biology of the Cardiovascular System*, UCLA Symposia on Molecular and Cellular Biology, Roberts and Schneider, Eds. Wiley-Liss, New York, 131:195–206; Hamilton et al., 1991, *Biochem. Biophys. Res. Comm.* 180:652), induction of acute phase proteins (Richards et al., 1992, *J. Immunol.* 148:1731), regulation of early gene expression (Liu et al., 1992, *Cell Growth and Diff.* 3:307) and induction of vasoactive intestinal peptide (Rao et al., 1992, *Neuro Report* 3:865).

Receptors of ~150,000 dalton molecular weight for OM have been characterized on a wide variety of cells (Horn et al., 1990, *Growth Factors* 2:157; Grove et al., 1991, *J. Biol. Chem.* 266:18194; Brown et al., 1991, *J. Immunol.* 147:2175; Linsley et al., 1989, *J. Biol. Chem.* 264:4282). It has recently been shown that OM specifically binds gp130, the IL-6 signal transducer (Gearing et al., 1992, *Science* 255:1434; Liu et al., 1992, *J. Biol. Chem.* 267:16763), and that antibodies to gp130 block OM—, LIF—, CNTF— (Liu et al., 1992, *J. Biol. Chem.* 267:16763; Taga et al., 1992, *Proc. Natl. Acad. Sci. USA* 89:10998) and IL-11 signalling (Yin et al., 1993, *J. Immunol.* 151:2555).

2.2. PROPERTIES OF INTERLEUKIN-6

IL-6 occupies a prominent position in the cytokine networks regulating cell growth, development of the hematopoietic and immune systems, and host responses to infection and injury (reviewed by Sehgal et al., 1987, *Science* 235:731). For example, IL-6 is capable of promoting T and B lymphocyte growth and differentiation (Garman et al., 1987, *Proc. Natl. Acad. Sci. USA* 84:769; Takai et al., 1988, *J. Immunol.* 140:508). Additionally, IL-6 has been reported to inhibit the proliferation of both cancer cells and human endothelial cells (May et al., 1989, *Biochem. Biophys. Res. Comm.* 159:991), and thereby would be expected to have antitumor activity either directly or by antagonizing the angiogenic process.

2.3. HEMATOPOIESIS

The hematopoietic system is regulated in a coordinated manner by the growth and differentiation of a variety of cell types from a population of progenitor cells. The development of hematopoietic cells is regulated by a complex array of environmental factors, including soluble protein mediators. Aberrations of composition of these cells occur in a variety of disease states (e.g., thrombocytopenia purpura) and as a consequence of the treatment of diseases (e.g., cancer chemotherapy, AZT treatment for AIDS). Agents that have restorative effects on hematopoiesis during these processes have the ability to alleviate the symptoms of disease, and allow more effective therapy.

3. SUMMARY OF THE INVENTION

The present invention relates to methods of using OM. In particular, it relates to the use of OM to stimulate the synthesis of IL-6 in target cells and in addition, it relates to the use of OM to treat cytopenias caused by certain disease states or by treatment regimens.

The invention is based, in part, on Applicants' discovery that human endothelial cells are stimulated by OM to produce IL-6. Thus, OM may be used as an IL-6-inducing agent on target cells such as human endothelial cells. As a result, the increased production of IL-6 may regulate cell growth, leukocyte differentiation, and inhibit tumor growth.

Furthermore, OM is also shown to induce thrombocytopoiesis, i.e. platelet production, both in vitro and in vivo. In addition, OM can reduce the severity of anemia induced by irradiation and cytotoxic drugs, and also allow higher doses of such drugs to be tolerated by a recipient. OM can also enhance the anti-tumor effects of these chemotherapeutic drugs when they are used in combination.

The invention is described by way of examples in which OM stimulates human umbilical vein endothelial cells to produce IL-6, which is assayed by its ability to inhibit the growth of human breast carcinoma cells. The in vivo administration of OM in mice, dogs and non-human primates is capable of enhancing platelet production. Additionally, OM accelerates the recovery of platelets in murine models of thrombocytopenia, and also reduces the severity of anemia in the same animals. Thus, a wide variety of uses for OM are encompassed by the invention described herein, including, but not limited to, induction of hematopoiesis, especially following therapeutic regimens that cause thrombocytopenia and anemia; promotion of wound healing; and inhibition of tumor growth as well as enhancing the activity and tolerated dosage of chemotherapy.

4. BRIEF DESCRIPTION OF THE DRAWINGS

FIG. 1 Time-dependent release of IL-6 from stimulated human umbilical vein endothelial cells. Confluent cultures were treated with (●) and without (▲) 100 ng/ml OM. Triplicate 200 µl aliquots of conditioned media were withdrawn at the indicated time intervals and the concentration of IL-6 determined by ELISA, as described in Section 6.1.3., infra (expressed in ng/ml). The standard error in these assays was 2%.

FIG. 2 Dose-dependent production of IL-6 from stimulated human umbilical vein endothelial cells. Confluent cultures were treated with varying doses of recombinant OM for 72 hours. Triplicate 200 µl aliquots of conditioned media were withdrawn and the concentration of IL-6 determined by ELISA. The amount of IL-6 released in ng was normalized for $10^6$ cells.

FIG. 3 Expression of IL-6 mRNA transcripts in OM-stimulated human umbilical vein endothelial cells. Cells were exposed to 100 ng/ml recombinant OM for 6 hours, then their RNA extracted. 5 ng samples of total cellular RNA were analyzed by Northern blot as described in Section 6.1.4., infra, Lane 1: positive control RNA; Lane 2: untreated HUVEC RNA; Lane 3: OM-treated HUVEC RNA.

FIG. 4A Increases in platelet counts in mice treated with OM. Female C3H/HeJ mice (8–10 weeks old) were obtained from the Jackson Laboratory (Bar Harbor, Me.). Mice (four animals per treatment regimen) were injected with 100 µl OM in PBS/BSA containing 15 µg (○), 5 µg (●), or 1.5 µg (Δ), intravenously via the tail veins. Control mice (■) were treated with diluent alone. Mice were treated twice daily for seven days. Mice were bled at indicated times via the retro-orbital sinus and complete blood counts including platelet count were enumerated. ←—→indicates treatment duration.

FIG. 4B Increase in platelet counts in mice treated with IL-6. Recombinant human IL-6 was produced in *E. coli* and purified as detailed by Burstein et al. (1992, *Blood* 80:420). The experiments were performed as described above for OM. Symbols are the same as for FIG. 4A.

FIG. 5 Effect of duration of OM treatment on platelet levels in mice. Groups of 5 mice were treated twice daily with 10 g/day OM for either 3 ■, 5 □ or 7 ▨ days. The vertical bars show the percentage increase in the platelet counts of pretreatment control values. Platelet counts were maximal 3 days following the cessation of each treatment regimen.

FIG. 6A and 6B Accelerated platelet recovery in irradiated mice treated with OM. Groups of 5 mice received either 500 Rads (FIG. 6A) or 250 Rads (FIG. 6B) of radiation. OM treatment was initiated 24 h later with either 30 µg/day or 15 µg/day in 100 µl PBS/BSA. Control mice were treated with vehicle only. OM was administered intravenously and continued daily for 15 days. On subsequent days, blood samples were drawn and analyzed as described in FIG. 4A PBS/BSA diluent (●), 15 µg/day (□), 30 µg/day (■) OM.

FIG. 7 Effects of OM on radiation induced anemia. C3H/HeJ mice received 500 Rads of γ irradiation. Twenty fours hours after irradiation the mice were treated intravenously with 30 µg per day of OM for fifteen days as in FIG. 6. Blood samples were taken from the orbital sinus and assayed for red blood cell counts. Control (□); OM treated (■).

FIG. 8 Effects of OM on thrombocytopenia induced by administration of Mitomycin C. C3H/HeJ mice were treated with 6 mg/kg Mitomycin C intravenously. One day following drug administration, treatment was initiated with twice daily injections of OM for 3 three-day periods each followed by a day's rest, for a total treatment period of eleven days. Blood samples were taken through the orbital sinus and platelet counts were determined. The results are expressed as a percentage of initial platelet number. Mitomycin C (6 mg/kg)–7.5 µg OM (■), Mitomycin C (6 mg/kg) alone (□).

FIG. 9 Effects of OM on the anti-tumor activity of Mitomycin C. Mice were injected subcutaneously with $1\times10^7$ A375 human melanoma cells. When tumors reached approximately 100 cubic millimeters, two groups of animals were treated with a single dose of Mitomycin C at 8 mg/kg. In one set of animals three days prior to receiving Mitomycin C a treatment regimen was started with OM comprising 15 µg per 12 hours for 20 injections (10 days). Measurements of the implanted tumors were taken weekly and data was reported as the mean tumor volume.

FIG. 10A and 10B Effects of OM on platelet number (FIG. 10A) and red blood cell counts (FIG. 10B) in a murine model. Animals were treated twice daily for 15 days either subcutaneously or intravenously with 7.5 µg of OM. Mitomycin C was given on day 1, 5 and 9. Blood samples were collected, and counted for platelets (FIG. 10A) and for red blood cells (FIG. 10B). 4 mg/kg Mitomycin C (●), 4 mg/kg Mitomycin C/OM given subcutaneously (▲), 4 mg/kg Mitomycin C/OM given intravenously (■), 2 mg/kg Mitomycin C/OM given intravenously (□), 2 mg/kg Mitomycin C (○), 2 mg/kg Mitomycin C/OM given subcutaneously (Δ).

FIG. 11A and 11B Effects of OM on platelet number and red blood cell counts in *Macaca facicularis* monkeys. Animals were treated with equal doses twice a day and retreated 4 to 6 weeks later as described in Table 3. Blood samples were taken from the animals and counted for platelets (FIG. 11A) and for red blood cells (FIG. 11B). 90 µg/kg/day×3, 86 µg/kg/day×3(□), 30 µg/kg/day×7, 30 µg/kg/day×3 (▲), 10 µg/kg/day×7, 30 µg/kg/day×3(○), control (●), OM treatment initiated (↑).

FIG. 12 Effects of OM dose on platelet levels in normal *Macaca mulatta* (Rhesus) monkeys. Female Rhesus monkeys were injected twice daily with OM at 30 µg/kg/day or 90 µg/kg/day over a period of seven days. Blood samples were removed and counted for platelets. OM 30 µg/kg/day (□), OM 90 µg/kg/day (■).

DETAILED DESCRIPTION OF THE INVENTION

Figure 1:
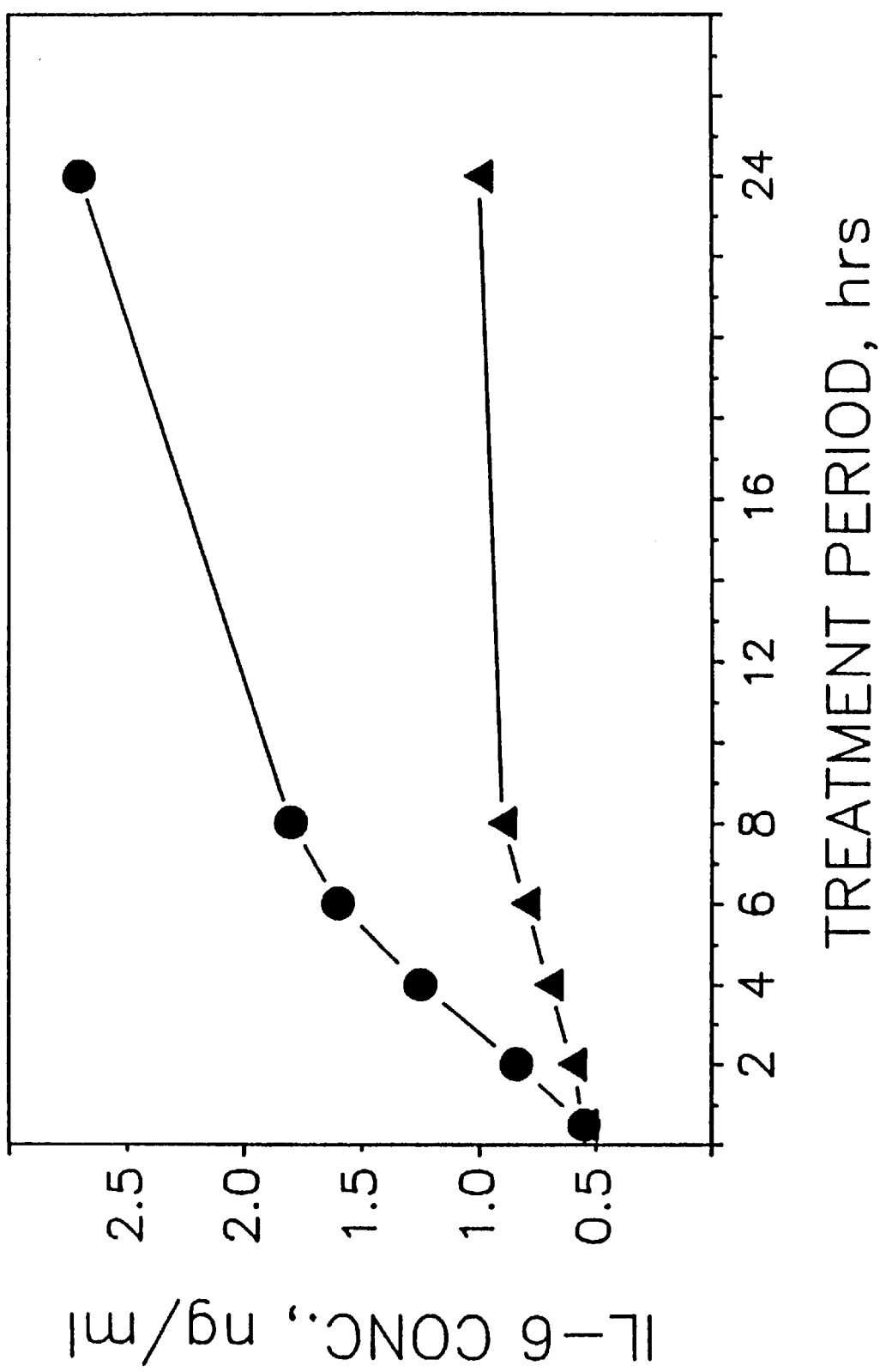

The present invention relates to methods of using OM. In particular, it relates to the use of OM to induce IL-6 synthesis in human endothelial cells. Furthermore, the invention relates to the use of OM alone or in combination with other cytokines to treat cytopenias by inducing hematopoiesis such as thrombocytopoiesis and erythropoiesis, and to allow higher doses of chemotherapy and radiation to be tolerated by a cancer patient. For the purpose of the present invention, the term "cytopenia" refers to a reduction of cellular elements in the circulating blood. Cytopenia may result from a variety of causes, and include both a general reduction of cell numbers in the blood as well as a specific reduction of a particular cell type, such as platelet reduction in thrombocytopenia, and red blood cell reduction in anemia.

The invention is discussed in more detail in the subsections below, solely for purposes of description and not by way of limitation. For clarity of discussion, the specific procedures and methods described herein are exemplified using cultured cell lines and in vivo animal models; they are merely illustrative for the practice of the invention. Analogous procedures and techniques are equally applicable to all mammalian species, including human subjects.

5.1. USES OF ONCOSTATIN M IN IL-6 INDUCTION

In the present invention, it is disclosed that OM is capable of inducing normal human endothelial cells to synthesize and secrete bioactive cytokines, such as IL-6 and GM-CSF. The effect of OM on IL-6 synthesis and secretion from human endothelial cells is both time and dose dependent. As described more fully in Section 6, infra, cultured human umbilical vein endothelial cells treated with OM respond rapidly by secreting increased levels of bioactive IL-6. In addition, this effect of OM is shown to act at the transcriptional level since OM-treated endothelial cells exhibit increased levels of IL-6 specific mRNA. Therefore, OM may be used as an IL-6-inducing agent on various cells including endothelial cells in situations where the increased production of IL-6 is desired, e.g., leukocyte proliferation and differentiation or tumor inhibition. IL-6 synthesis and secretion may be induced systemically by the introduction of OM to the circulatory system or may be targeted to specific tissues using techniques known in the art, including but not limited to topical administration, injection, or through the use of target specific compounds directly linked to OM.

5.2. USES OF ONCOSTATIN M IN PLATELET PRODUCTION

The present invention, described herein in Sections 7 and 8, infra, shows that in vivo OM administration increases platelet production in normal animals and thrombocytopenic animals over a large dose range without any apparent toxicity, and with modulation of other hematopoietic cells. This indicates that OM may have important clinical applications in humans, as it may enhance megakaryocyte proliferation and maturation as well as platelet production and reduction of anemia, when used alone or in combination with IL1-9.

OM alone is capable of accelerating the platelet recovery in mice rendered thrombocytopenic by irradiation. It is possible that OM is accelerating megakaryocyte maturation in this model and/or inducing the production of other factors such as colony stimulating factors which are capable of providing an increase in the progenitor cell pool. However, the "apparent" lack of detrimental effects on other cell lineages in normal recipients, unlike that for IL-6 and IL-11, is noteworthy and suggests a unique mechanism for OM effects in vivo.

The potent biological activity of OM in stimulating platelet production suggests its use in a wide variety of clinical conditions, especially those that are accompanied by a decrease in platelet levels. Thrombocytopenia is generally defined as a decrease in platelet count, which may be due to decreased platelet production, increased platelet destruction, or sequestration. A large number of agents and conditions are known to cause thrombocytopenia, including malignancy, bone marrow transplantation, chemicals, drugs, radiation, viral infection and genetic abnormality. Thus, it is within the scope of the present invention that OM is used alone or in combination with other cytokines to induce thrombocytopoiesis in conditions where platelet levels are below normal or where higher platelet counts are desirable, irrespective of the underlying etiology of the disorders.

It is particularly noteworthy that conventional cancer therapy involving chemotherapeutic drugs and radiation often leads to platelet toxicity, thereby substantially reducing platelet levels in patients undergoing treatment. For example, a number of anticancer compounds have been shown to induce such adverse effects, and they include many common drugs. Therefore, OM may be used prior to, simultaneous with or after the administration of radiation therapy and/or chemotherapeutic drugs, including but not limited to, mitomycin, fluorouracil, doxorubicin, cyclophosphamide, methotrexate, vinblastine, vincristine, daunorubicin, cisplatin, and the like. The ability of OM to induce platelet production may further allow the use of chemotherapeutic agents and radiation at higher than normal doses alone or in combination with bone marrow transplantation or in combination with peripheral blood stem cells.

It should be noted that OM may not affect all hematopoietic cell lineages, since its in vivo administration does not affect the levels of other hematopoietic cell lineages in normal animals (See Section 7, infra). Thus, OM may be used in combination with other cytokines which have positive effects on other hematopoietic cell lineages. Such cytokines include the various interleukins (IL1-15), especially IL-3, and various colony-stimulating factors, especially stem cell factor, Flk-2, G-CSF, GM-CSF, LIF and erythropoietin. Further, OM may have additive effects or even synergize with such cytokines on platelet production, including thrombopoietin.

5.3. ADMINISTRATION OF ONCOSTATIN M

For the practice of the present invention, OM may be obtained by recombinant DNA technology (Malik et al., 1989, *Mol. Cell. Biol.* 9:2847; Sambrook et al., 1989, *Molecular Cloning: A Laboratory Manual,* Cold Spring Harbor Laboratory, N.Y.), purification from natural cellular sources (Zarling et al., 1986, *Proc. Natl. Acad. Sci. USA* 83:P739), chemical synthetic techniques (Creighton, 1983, *Proteins Structures and Molecular Principles,* W. H. Freeman and Co., N.Y.; Stewart and Young, 1984, *Peptide Synthesis,* 2nd ed., Pierce Chemical Co.), or any other methods that are well known in the art. OM may be used in recombinant or natural form or as biologically active fragments or receptor binding mimetics. Techniques for formulation and administration may be found in *"Remington's Pharmaceutical Sciences",* 18th ed., 1990, Mack Publishing Co., Easton, Pa.

Preferably, OM is formulated and administered systemically. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and the like. Most preferably, administration is intravenous. For injection, OM may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Effective concentrations and frequencies of dosages of OM to be administered may be determined through procedures well known to those in the art, which address such parameters as biological half-life, bioavailability, and toxicity. A preferred dosage concentration may range from about 0.01 mg/kg body weight to about 20 mg/kg body weight. A single administration of OM may be sufficient to maintain the required circulating concentration but multiple doses may be necessary to establish and maintain the requisite concentration in circulation.

OM may be administered to patients alone or in combination with other therapies. Such therapies include the sequential or concurrent administration of cytokines, drugs, radiation and antibodies. Since the dosage and frequency of such combined therapies with OM may be different from the use of OM alone, appropriate tests must be performed in order to determine the best dosage when more than one class of therapeutic agents is to be administered.

6. EXAMPLE: ONCOSTATIN M-INDUCED STIMULATION OF INTERLEUKIN-6 SYNTHESIS IN HUMAN ENDOTHELIAL CELLS

6.1. MATERIALS AND METHODS

6.1.1. PREPARATION OF HUMAN UMBILICAL VEIN ENDOTHELIAL CELLS

First passage cultures of human umbilical vein endothelial cells (HUVECs) were obtained from Cell Systems (Kirkland Wash.) as prepared according to the method of Wall et al., 1978, *J. Cell. Physiol.* 96:203. Cells were passaged with collagenase and grown to confluence on gelatin-coated plasticware in CS-1 defined serum-free medium (Cell Systems) supplemented with heparin and recombinant ECGS (Bionetics). Cells were given fresh unsupplemented medium at least 12 hours prior to experimentation.

6.1.2. GROWTH INHIBITION ASSAY

The breast carcinoma cell line, ZR-75-30, was obtained from the American Type Culture Collection, Rockville, Md. (catalog #CRL 1504). Cells were cultured in Dulbecco's minimal essential medium (GIBCO) supplemented with 10% fetal bovine serum (Hyclone). Cells were plated at $1 \times 10^4$ cells/50 $\mu$l/well in 96-well tissue culture plates (Falcon). Following a 4 hour incubation at 37° C., cells were treated with test samples in triplicate. After 48 hours incubation, cells were treated with 50 $\mu$l of medium containing 0.05 $\mu$Ci of 5-[$^{125}$I]-iodo-2' deoxyuridine (Amersham) and incubated an additional 24 hours. Monolayers were washed with Phosphate Buffered Saline (PBS), fixed in 95% menthol, air-dried, and incorporated radioactivity was solubilized in 200 $\mu$l IN NaOH. DNA synthesis was measured by quantitating the amount of radiolabeled nucleotide incorporation into the DNA of actively growing cells. After 72 hours treatment, unlabeled cells were trypsinized and counted using a hemacytometer, indicating that the amount of radioactivity was directly proportioned to the total number of cells in the well.

6.1.3. QUANTITATIVE MEASUREMENT OF IL-6 RELEASED FROM HUMAN UMBILICAL VEIN ENDOTHELIAL CELLS

A "sandwich" enzyme-linked immunosorbant assay (ELISA) for the quantitative determination of human IL-6 in tissue culture media, sera, and other fluids was commercially obtained from Research and Diagnostic Systems (Minneapolis, Mn.) and performed according to their recommended procedure. Briefly, samples were pipetted into microtiter plate wells which had been coated with an IL-6-specific monoclonal antibody and the IL-6, if any, was bound by the immobilized antibody. After washing away any unbound sample proteins, an enzyme-linked polyclonal antibody specific for IL-6 was added to the wells and allowed to bind to any IL-6 bound during the first incubation. Following a wash to remove any unbound antibody-enzyme reagent, a substrate solution was added to the wells causing color to develop in proportion to the amount of IL-6 bound in the initial step. Color was monitored at 405 nM on a spectrophotometer and compared to the value for a known amount of IL-6 from a standard curve. Individual samples were run in duplicate, with a standard error of +2%. The minimal detectable dose of IL-6 was 3.5 pg/ml.

6.1.4. PREPARATION OF TOTAL CELLULAR RNA FROM HUMAN UMBILICAL VEIN ENDOTHELIAL CELLS AND NORTHERN BLOT

Total cellular RNA was isolated by lysing HUVECs in guanidium isothiocyanate followed by recovery of RNA by centifugation through cesium chloride (Sambrook et al., 1989, *Molecular Cloning: A Laboratory Manual,* Cold Spring Harbor Laboratory, Cold Spring Harbor, N.Y.). Then, 5 $\mu$g/sample were fractionated on 1.2% agarose gel with 6% formaldehyde and blotted onto nylon membranes (Hybond-N, Amersham) for Northern blot analysis. RNA from a lung carcinoma cell line, H2981, was used as a positive control for IL-6 expression. Hybridization was performed at 37° C. in a solution containing 50% formamide, 50 mM sodium phosphate pH7.0, 5×SSC, 100 $\mu$g/ml denatured salmon sperm DNA, 10×Denhardt's solution and $5 \times 10^5$–$10^6$ dmp/ $\mu$g/ml of labeled IL-6 exon-specific oligonucleotide probe (catalog #BPR 32, Research and Diagnostic Systems, Minneapolis, Mn.). This particular probe was specific for 4 separate exon regions of the IL-6 gene and was labeled at the 5' end to a specific activity of $4.2 \times 10^9$ dmp/$\mu$g using a T4 polynucleotide kinase and $\gamma$-$^{32}$p-ATP labeling procedure as recommended by Research and Diagnostic Systems. After hybridization was complete, the membrane was washed in 6 ×SSC+0.1% SDS at 30° C. for 20 minutes. The membranes were then exposed to x-ray film with an intensifying screen at -70° C. for 48 hours.

6.2. RESULTS 6.2.1. IL-6 BIOACTIVITY FROM ONCOSTATIN M STIMULATED ENDOTHELIAL CELLS: INHIBITION OF HUMAN BREAST CARCINOMA CELL GROWTH

Confluent cultures of human umbilical vein endothelial cells (HUVECs) were treated with and without 100 ng/ml recombinant OM for 72 hours. The conditioned media (CM) was collected, clarified by centrifugation and stored at -20° C. prior to use. The growth of human breast carcinoma cells, ZR-75-30, was monitored by using the growth inhibition assay described in Section 6.1.3., supra, following treatment with recombinant OM, recombinant IL-6, the CM from untreated HUVECs, the CM from OM-treated HUVECs and the CM from OM-treated HUVEcs preincubated for 1 hour at 37° C. with anti-IL-6 neutralizing antibodies. The results of this experiment are presented in Table 1.

Recombinant OM demonstrated no significant inhibitory effect on the growth of ZR-75-30 cells (14%), whereas a ten-fold lower dose of recombinant IL-6 was highly active in this regard (88%). These results indicate that ZR-75-30 cells were considerably less sensitive to growth inhibition by OM than by IL-6. HUVEC CM (1:40 dilution) was also ineffective at inhibiting the growth of ZR-75-30 cells (8%), while the CM from OM-treated HUVECs (1:40 dilution) demonstrated a dramatic growth inhibitory effect (70%). The results indicate that OM treatment stimulated the release of a tumor cell suppressor molecule from HUVECs which, in contrast to OM, acted directly to inhibit the growth of the breast carcinoma cells. When the CM from OM-treated HUVECs was preincubated with neutralizing antibodies to IL-6 (anti-IL-6), the inhibitory activity of the sample was completely blocked. Therefore, the tumor cell suppressor molecule induced by ON was immunologically identical to IL-6.

TABLE 1

IL-6 BIOACTIVITY ON ZR-75-30 BREAST CARCINOMA CELLS[1]

| Sample | [$^{125}$I]-IUdR Incorporation | % Inhibition |
|---|---|---|
| medium alone | 11,852 +/− 324 cpm | 0 |
| OM, 25 ng/ml | 10,088 +/− 527 | 14 |
| IL-6, 2.5 ng/ml | 1,467 +/− 86 | 88 |
| CM alone | 10,855 +/− 5 | 8 |
| OM/CM | 3,703 +/− 162 | 70 |
| OM/CM + Anti-IL-6 | 10,892 +/− 207 | 8 |

[1]ZR-75-30 cells were treated for 72 hours in the presence of 10% fetal bovine serum. Cell proliferation was measured according to Section 6.1.2., supra, and is presented in the table as percent (%) inhibition [cpm of medium alnone-cpm of sample/cpm of medium alone] × 100. Conditioned medium (CM) was diluted 1:40 to minimize serum dilution in the bioassay. Anti-IL-6 was used at a concentration of 25 μg/ml.

6.2.2. TIME AND DOSE REQUIREMENTS FOR ONCOSTATIN M STIMULATION OF IL-6 ACTIVITY IN ENDOTHELIAL CELLS

Aliquots of the CM from HUVECs were taken at various time intervals following treatment with 100 ng/ml OM. Samples were measured for IL-6 content utilizing the ELISA procedure described in Section 6.1.3., supra. As shown in FIG. 1, increases in IL-6 levels were observed as early as 2 hours post-treatment, and continued throughout the 24 hour period without reaching a maximal level. By 8 hours, IL-6 concentration in HUVEC media had risen from 0.8 ng/ml to 1.8 ng/ml, and to 27 ng/ml by 24 hours. These kinetics indicated a rapid response by HUVECs to OM treatment.

Figure 2:
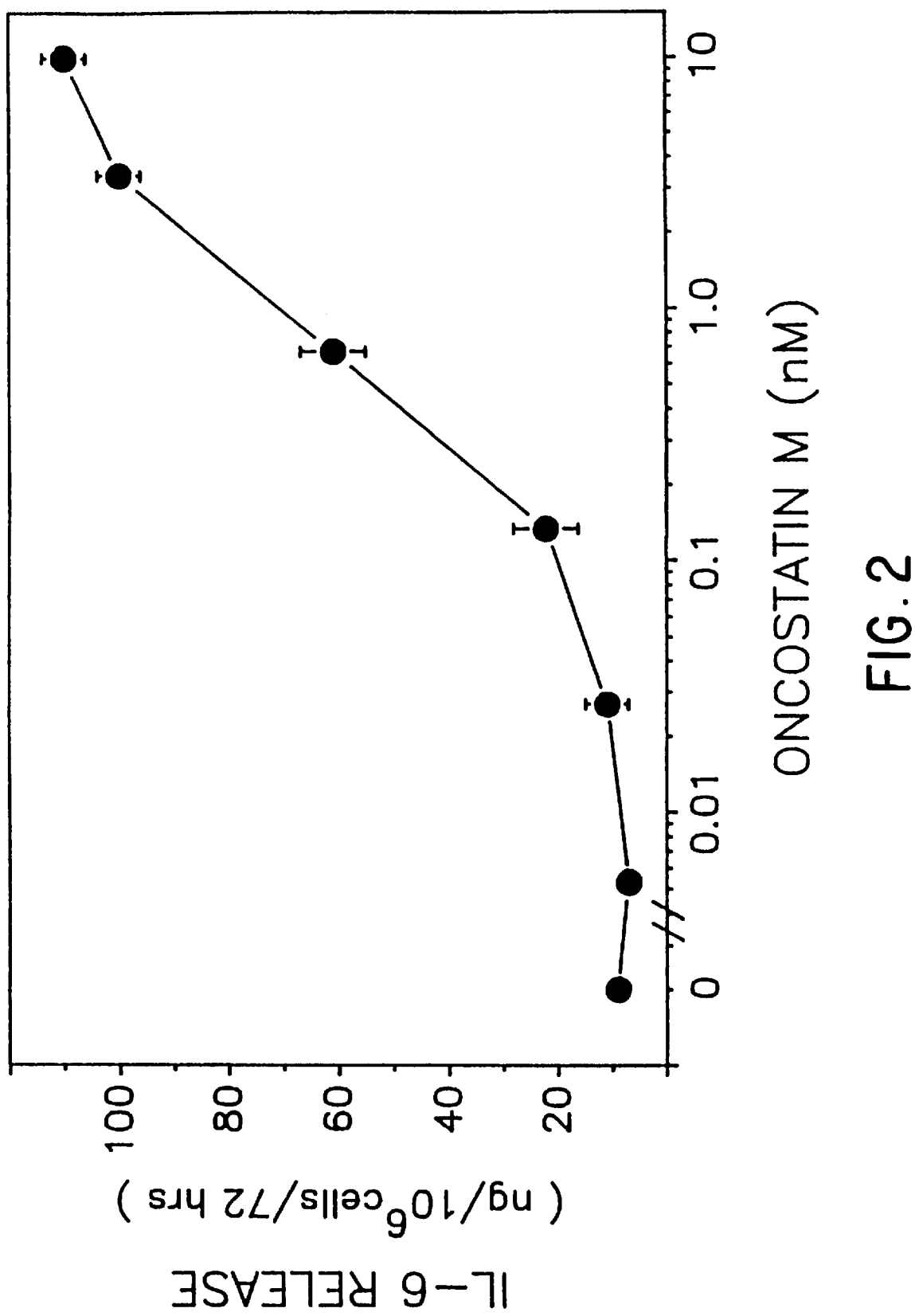

FIG. 2 demonstrates the dose-dependent action of OM on HUVECs when measured at 72 hours post-treatment, at which point the IL-6 content of CM had risen from 10 ng/10$^6$ cells to 110 ng/10$^6$ cells (>10-fold). The effective dose for OM ranged from 0.1 nM (3 ng/ml) to 10 nM (300 ng/ml) with a half-maximal response, $ED_{50}$, of 15–30 ng/ml. Therefore, OM stimulated the release of immunoreactive IL-6 molecules from HUVECs in both a time and dose dependent manner.

6.2.3. ONCOSTATIN M INDUCED EXPRESSION OF IL-6 mRNA IN HUMAN UNBILICAL VEIN ENDOTHELIAL CELLS

Figure 3:
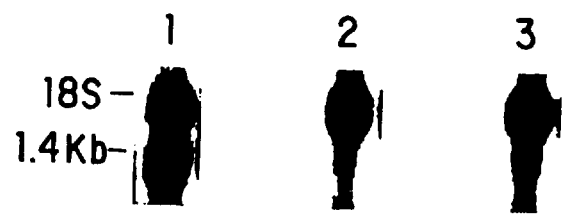

HUVECs were treated with and without 100 ng/ml recombinant OM and incubated at 37° C. for 6 hours. Cells were washed, solubilized, and their total RNA extracted as described in Section 6.1.4., supra. Total RNA from the human lung carcinoma cell line, H2981, was extracted and used as a positive control for expression of IL-6 mRNA. Northern blot analyses, performed as described in Section 6.1.4, supra, indicated that OM significantly amplified IL-6 mRNA levels (FIG. 3). Lane 1, FIG. 3, shows the 1.4 Kb mRNA species found in the positive control cell line, H2981. Lane 2, FIG. 3, indicates the low constitutive expression of IL-6 mRNA in untreated HUVECs. Lane 3 shows a significant amplification of IL-6 mRNA transcripts following OM treatment (5-fold). Therefore, OM induced the expression of higher levels of IL-6 MRNA in HUVECs, thus providing a molecular mechanism for the observed increases in IL-6 levels found in the CM of OM-treated HUVECS.

7. EXAMPLE: ONCOSTATIN M IS A POTENT THROMBOCYTOPOIETIC FACTOR

7.1. MATERIALS AND METHODS

7.1.1. ANIMALS AND REAGENTS

Female C3H/HeJ mice aged 8–10 weeks were obtained from The Jackson Laboratory (Bar Harbor, Me.). Recombinant human OM was expressed in Chinese Hamster ovary cells and purified as previously described. For all studies OM formulated at 1 mg/ml in 40% acetonitrile+0.05% TFA and stored at −20° C. was used. Prior to use, the oncostatin M was prepared for dosing by drying down the stock solution of OM with BSA as a carrier protein and then resuspending in PBS plus 1:1 BSA prior to use. Blood cell count analysis was performed using a Serono-Baker System 9000 automated cell counter using parameters for mice provided with the instrument. Irradiation was performed using a Mark I Cesium-137 irradiator (J. L. Shepherd & Associates, San Fernando, Calif.).

7.1.2. MEGAKARYOCYTE COLONY ASSAY

Marrow for the assay was prepared as described (Ishibashi et al., 1989, Proc. Natl. Acad. Sci. USA 86:5953). Marrow cells were enriched for progenitors on 1.077 g/cm$^3$ Ficoll gradient, followed by a 2-hr plastic adherence. Megakaryocytic colony-forming cells (CFU-MK) were assayed by culturing the enriched marrow cells (2×10$^4$ cells/ml) in IMDM rendered semi-solid with 0.9% methylcellulose and supplemented with 15% horse serum, 1×10$^{-5}$ M β-mercaptoethanol and 10% WEHI-3 conditioned medium (a source of murine IL-3). Megakaryocyte colonies (≧3 cells/colony) were enumerated following 5–6 days incubation at 37° C. in a 95% air–5% $CO_2$ tissue culture incubator.

7.1.3. INTRAVENOUS ADMINISTRATION

OM was prepared as above. Groups of four mice were injected with 100 μl of PBS/BSA solutions containing either 150 μg/ml, 50 μg/ml or 15 μg/ml of OM i.v. via the tail vein. Mice were treated twice daily for seven days. On subsequent days, blood was drawn from the orbital sinus, diluted, and complete blood counts analyzed as above. Control mice were treated with diluent alone.

7.1.4. OSMOTIC PUMP

Human recombinant OM (0.1 TFA/40% $CH_3CN$) 1 mg/ml was diluted 1:1 with PBS/BSA (1 mg/ml), lyophilized and resuspended at 1 mg/ml in PBS with BSA added at 417 μg/ml. Osmotic pumps (7 day, 1 μl/hr) were then implanted subcutaneously into the flank of groups of three mice. Mice were then bled at the times described via the retro-orbital sinus and analyzed for platelet number. Control mice were implanted with pumps containing the PBS/BSA diluent.

7.1.5. ENHANCEMENT OF PLATELET RECOVERY BY ONCOSTATIN M TREATMENT FOLLOWING SUB-LETHAL IRRADIATION

Groups of four mice (strain C3H/HeJ) received 500 Rads of radiation. Treatment was initiated 24 hours later with once daily i.v. injections of OM either 30 μg/day or 15 μg/day for 15 days. On subsequent days, blood samples were withdrawn via the orbital sinus, diluted and analyzed. Control mice were injected by the same regimen with diluent.

7.1.6. INHIBITION OF IRRADIATION INDUCED ANEMIA

Groups of four mice (strain C3H/HeJ) received 500 Rads of radiation. Treatment with a once daily i.v. dose of 30 μg of OM or a diluent was started 24 hours after the irradiation and continued for fifteen days. On subsequent days, blood samples were withdrawn via the orbital sinus, diluted and analyzed. Control mice were injected by the same regimen with diluent and the number of red blood cells was determined by cell counts.

7.1.7. EFFECT OF ONCOSTATIN M ON CHEMOTHERAPY INDUCED THROMBOCYTOPENIA

Groups of five mice (strain C3H/HeJ) were rendered thrombocytopenic by cytotoxic insult using mitomycin C(MMC). Mitomycin C was injected intravenously with a single dose of 2 mg/kg, 4 mg/kg or 6 mg/kg on days 1, 5 and 9. One day following MMC administration, treatment with OM was initiated on a schedule of 15 μg/day divided into two daily i.v. injections. Animals were treated for three, three-day cycles with one day rest between cycles or daily for 15 days. Blood samples were removed via the orbital sinus and analyzed for the number of platelets and red blood cells.

7.1.8. ANTI-TUMOR ACTIVITY OF ONCOSTATIN M WHEN COMBINED WITH MITOMYCIN C

Groups of seven mice (athymic nude) were implanted subcutaneously with $1 \times 10^7$ cells of human melanoma cell line A375 (ATCC CRL 1619). When the tumors reached approximately 100 mm³, animals were treated with a single dose of mitomycin C (MMC) at its maximum tolerated dosage (8 mg/kg) either alone, or in combination with OM (15 (g/12 hours×20) initiated three days prior to drug treatment. Mitomycin C was administered at 10 days post implant. Measurements of the implanted tumors were taken weekly and data reported as mean volume.

7.2. RESULTS

In order to study the in vitro and in vivo properties of OM, several indications were examined in vitro and in murine models. First, nude mice were implanted with a cell line previously transfected with the human OM gene that produced and secreted high levels of OM protein. Mice receiving OM for extended periods were monitored and examined histologically. This treatment was generally well tolerated by the animals; however, some notable changes were observed. Most notably, a localized vasodilation occurred around the tumor implant shortly after implantation and continued for the duration of the treatment. The mice also experienced cachexia and splenomegaly. The increase in spleen cell number was shown to be a result of megakaryocytosis in this organ. As a result of the above observation, the effects of human recombinant OM on megakaryocyte and platelet production were examined.

Figure 4A:
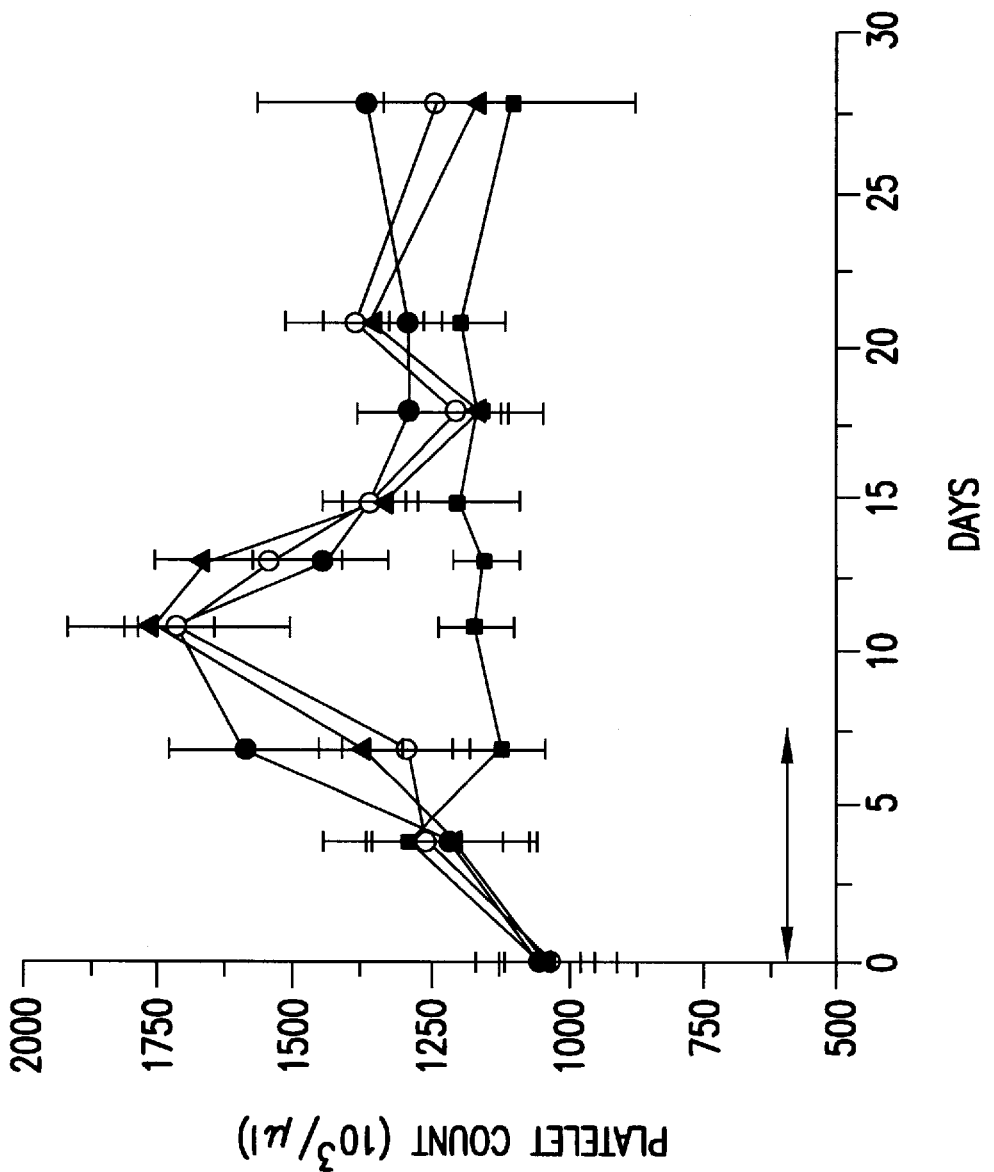

To evaluate the effect of recombinant OM on platelet production, in vivo studies were carried out in mice. Groups of five mice were treated with various dosages of OM intravenously twice daily for seven days as presented in FIG. 4A. At the highest dosage tested (30 μg/day) platelet levels were significantly increased over controls when measured at day 7 (p=0.001) and at all dosages tested, there were significant increases by day 11 (p≧0.005). After day 11, platelet numbers started to decline, and reached the level of control mice (vehicle only) by day 17. A greater than 50% increase in platelet count was observed at all dosages tested with no significant change in white or red blood cell numbers. In control mice, there was no significant change in platelet, white, or red blood cell numbers. A similar increase in circulating platelets occurred when OM was administered as a continuous infusion using an osmotic pump to deliver OM at a dose of 10 μg/day. OM also markedly increased platelet levels in normal dogs in a dose dependent fashion, while red blood cell counts were unaffected.

Figure 4B:
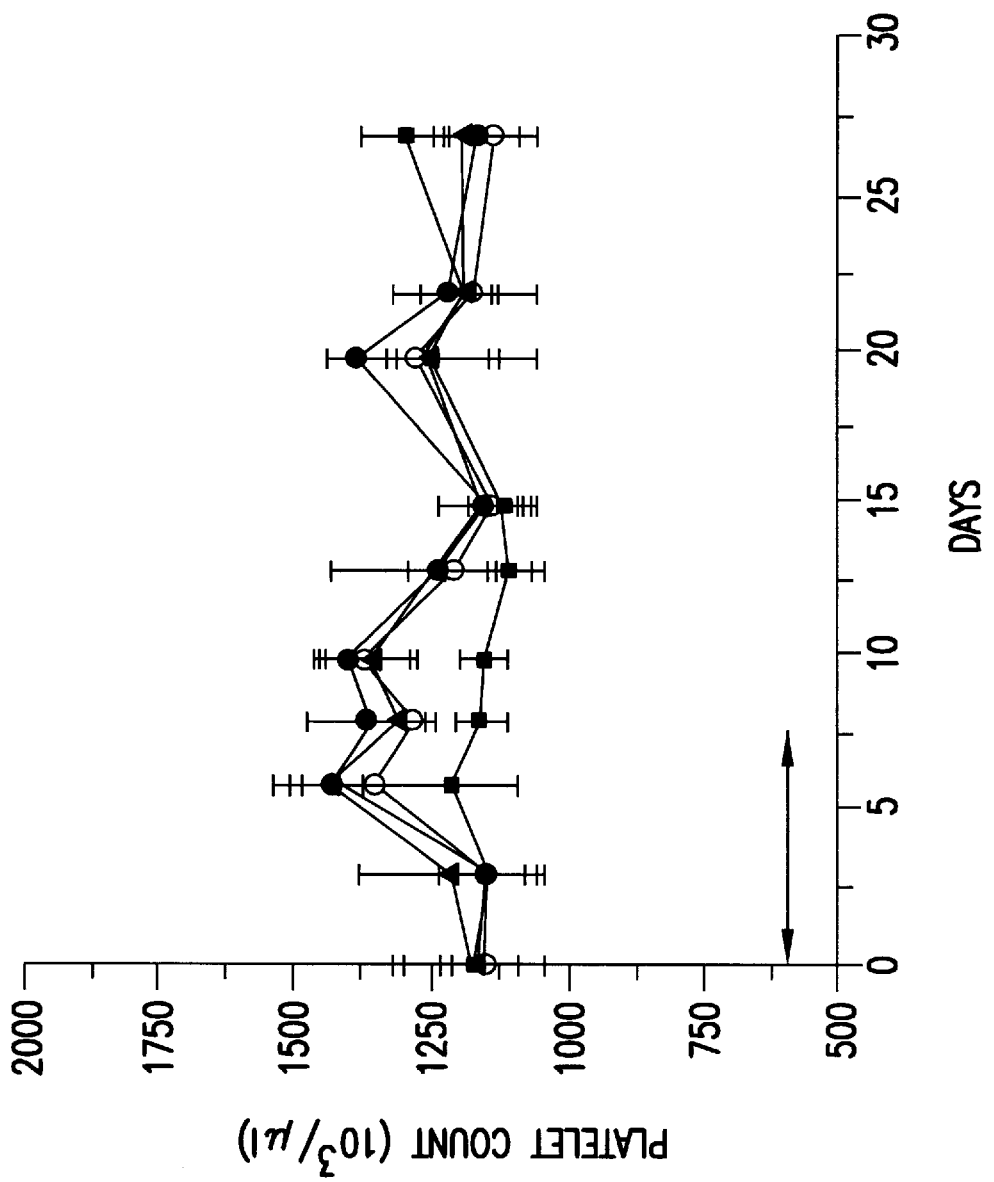

Because OM elicits the production of IL-6, a known thrombocytopoietic factor (Gordon et al., 1992, Blood 80:302), both in vitro (Brown et al., 1991, J. Immunol. 147:2175) and in vivo, the effects of these two cytokines were compared. FIG. 4B shows that at its maximally effective dose, IL-6 was able to evoke a 30% elevation in platelet count between days 6 and 10 in mice following treatment. OM as described above appeared to elevate platelet production in a manner distinct from IL-6, indicating an independent mechanism of action.

Figure 5:
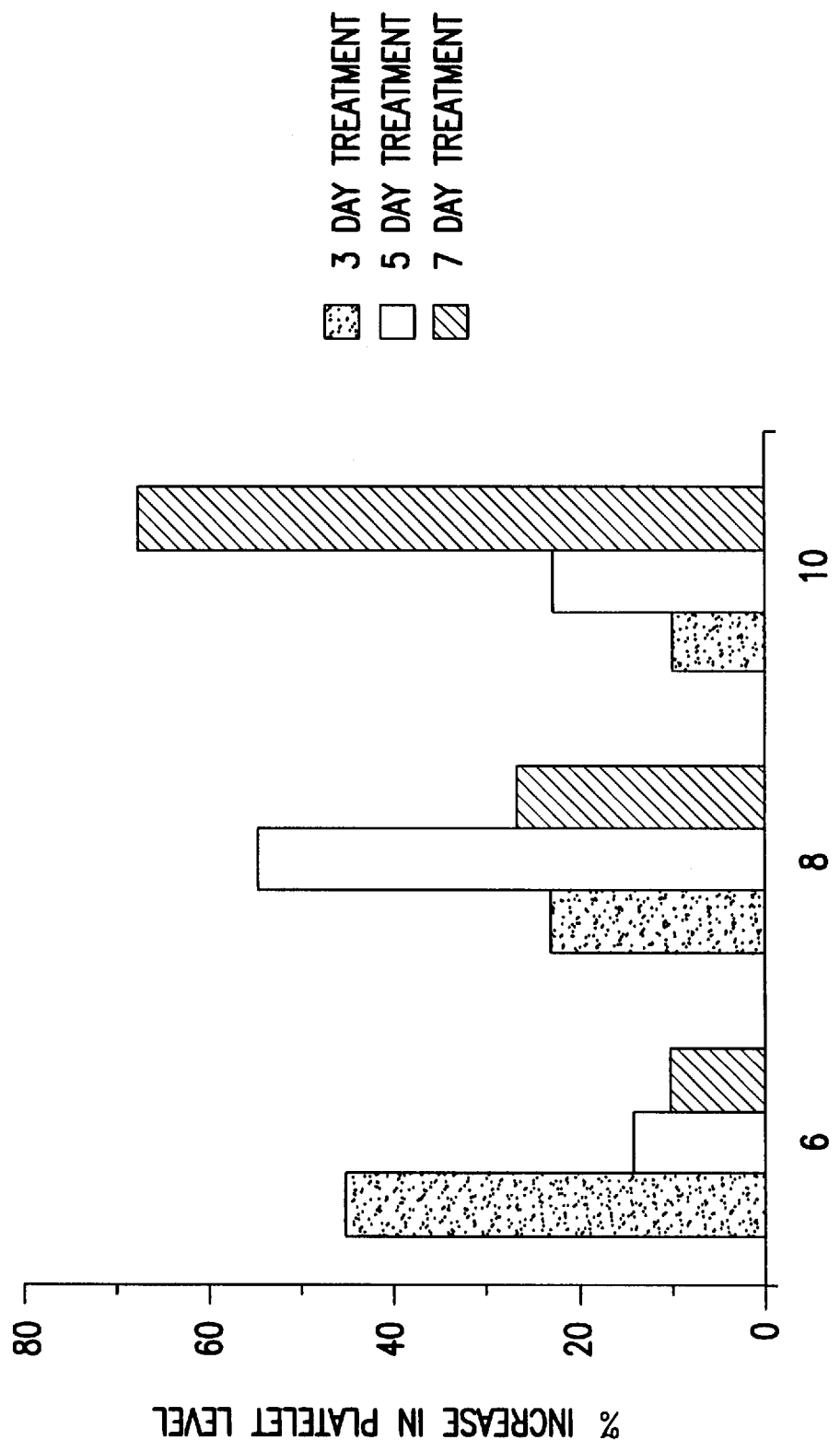

Since the maximal elevation of platelet number was seen after the cessation of OM treatment, the effects of the duration of OM treatment on platelet levels were examined to investigate the possibility that OM might regulate both megakaryocyte maturation and the production of platelets. OM was administered twice daily to a total dosage of 10 μg for 3, 5 or 7 days and the percentage increase in the number of platelets compared (FIG. 5). In contrast to the results obtained with treatment for 7 days, the maximal platelet levels following shorter treatment times were obtained at day 6 or 8 and were consistent with earlier findings of maximal levels seen 2–3 days after cessation of OM treatment. These findings were consistent with the hypothesis that OM modulated the production of platelets and that continuing treatment beyond three days reduced platelet levels at day 6 as compared to treatment that ended at day 3. This was also true when treatment for five days was compared to treatment for seven days. The cessation of OM treatment was followed by a rapid increase in platelet levels in both cases.

In vitro effects of OM on murine megakaryocyte colony formation from partially purified bone marrow cells were evaluated and the results are shown in Table 2. The ability of OM to effect colony formation alone and in combination with a panhematopoietin, IL-3 (Ihle et al., 1983, J. Immunol. 131:282) in the form of WEHI-3 cell conditioned medium was evaluated. While OM alone was unable to produce colonies of megakaryocyte lineage in semi-solid culture, it was able to increase both the number and size of colonies when combined with WEHI-3 cell conditioned medium. These effects are analogous to those obtained with IL-6, indicating that OM is a maturation factor that potentiates the effects of IL-3, but does not possess an intrinsic colony-stimulating capacity.

TABLE 2

REGULATION OF MEGAKARYOCYTE DEVELOPMENT BY OM

| CYTOKINE | CFU-Mk |
|---|---|
| Control | 0 |
| WEHI-3 CM | 13 ± 1 |
| IL-6 | 2 ± 1 |
| OM | 0 ± 1 |
| WEHI-3 CM + IL-6 | 30 ± 3 |
| IL-6 + OM | 3 ± 1 |
| WEHI-3 CM + OM | 31 ± 4 |
| WEHI-3 CM + IL-6 + OM | 32 ± 3 |

Figure 6A:
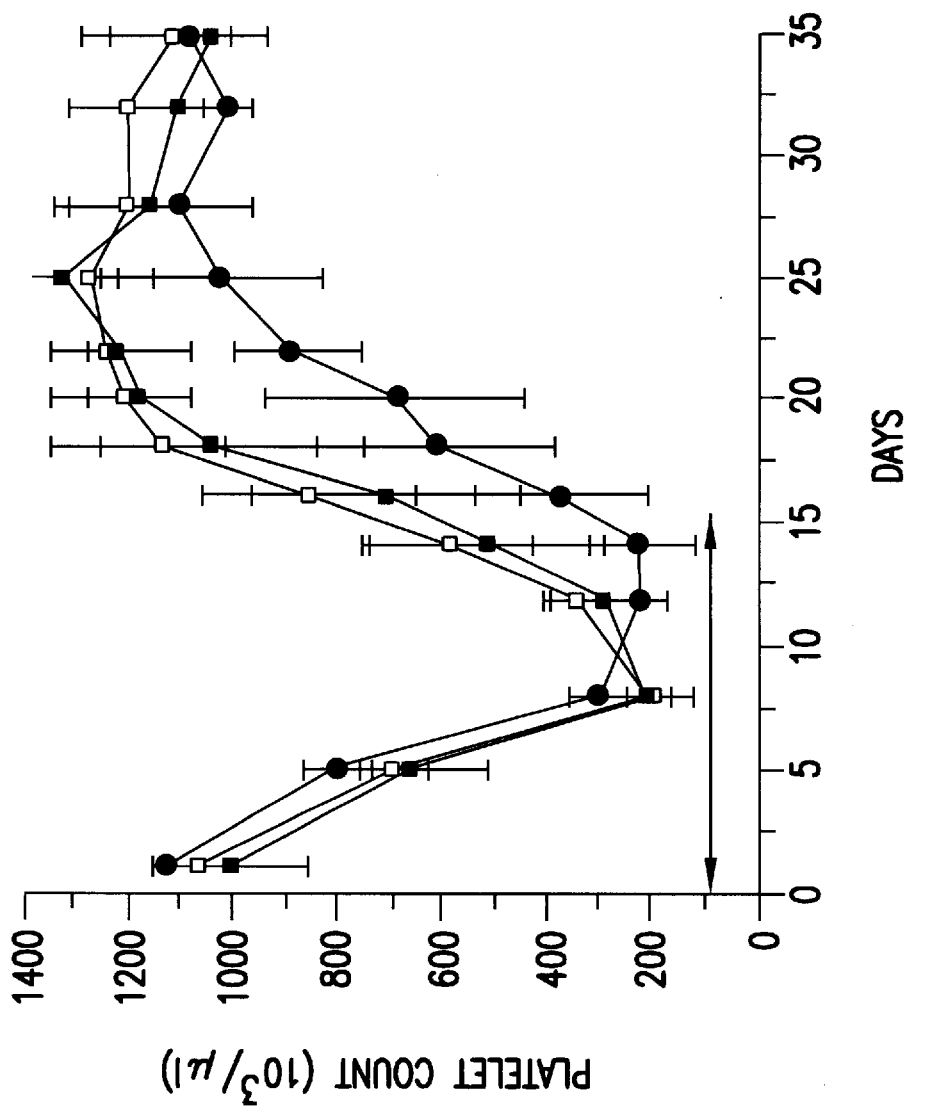
Figure 6B:
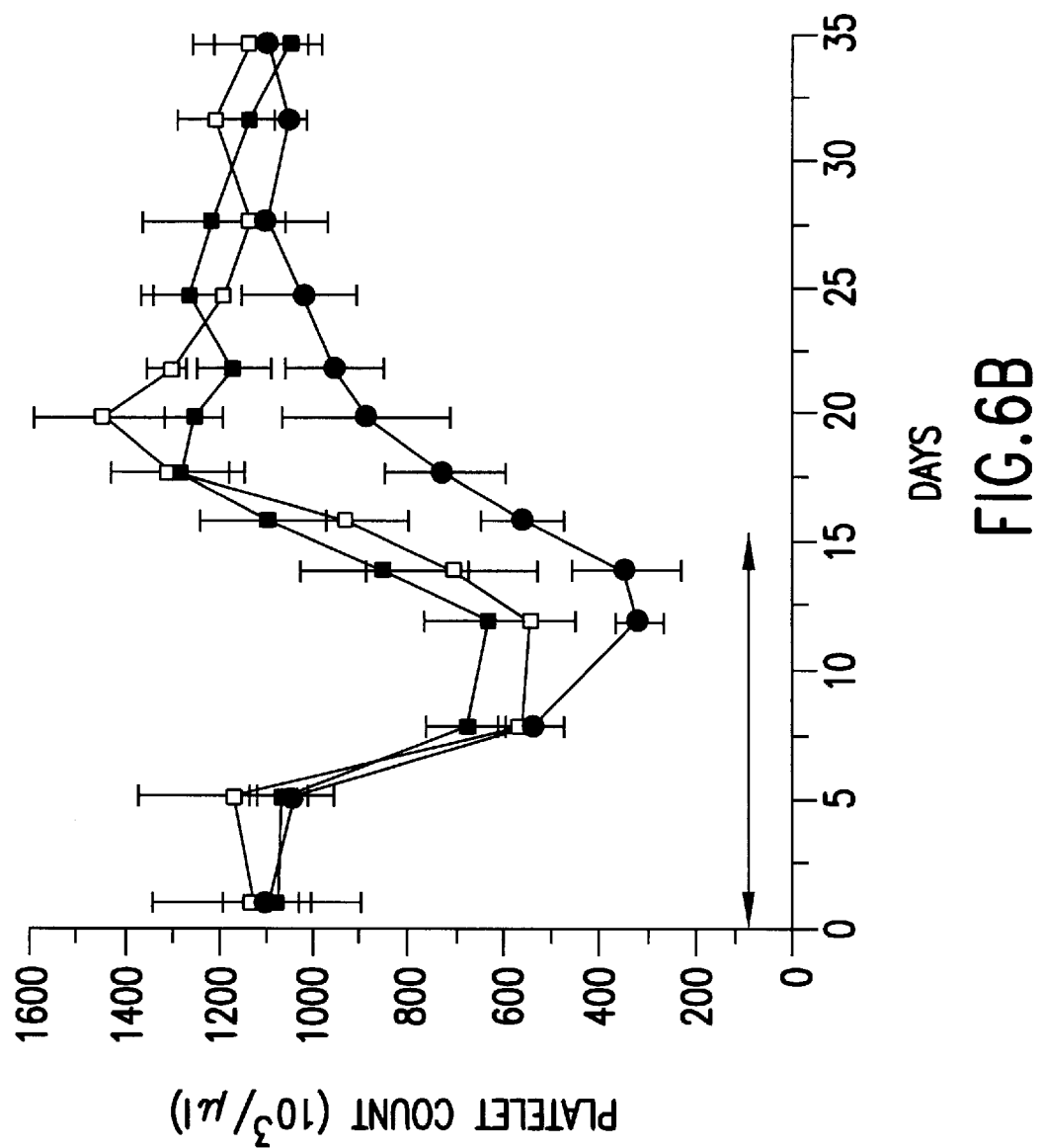

The activity of OM in thrombocytopenia was also tested in the murine model by measuring the effect of OM on platelet recovery in sublethally irradiated mice. In this study, mice were irradiated with 250 or 500 Rads of gamma-irradiation. Treatment with OM was initiated one day following irradiation, with the mice receiving daily intravenous doses of 15 or 30 µg/day for 15 days. Mice receiving 500 Rads of radiation had platelet counts reaching a nadir of $200 \times 10^3$ platelets/cubic millimeter (PLT/cmm) at about day 13 (FIG. 6A) following irradiation. Platelets returned to normal levels by day 25. At either dose of OM tested, the nadir of platelet counts in the treated animals to those untreated was similar at $200 \times 10^3$ PLT/cmm, but this level was reached at day 7 and was followed by an accelerated recovery of circulating platelets which reached pre-irradiation levels by at least day 18, followed by a slight increase in platelets above normal levels, and then a return to normal levels a few days later. At the lower irradiation dose of 250 Rads, platelet levels of the OM treated groups never dropped below $500 \times 10^3$ PLT/cmm (FIG. 6B). These animals as described above had an accelerated platelet recovery phase, by at least day 18, followed by a short increase in platelet numbers above normal and a subsequent drop to normal numbers. The platelet count in control mice receiving radiation treatment returned only to pre-irradiation numbers, whereas platelet numbers at the zenith of recovery in treated animals was approximately 125% of that of preirradiation levels.

Figure 7:
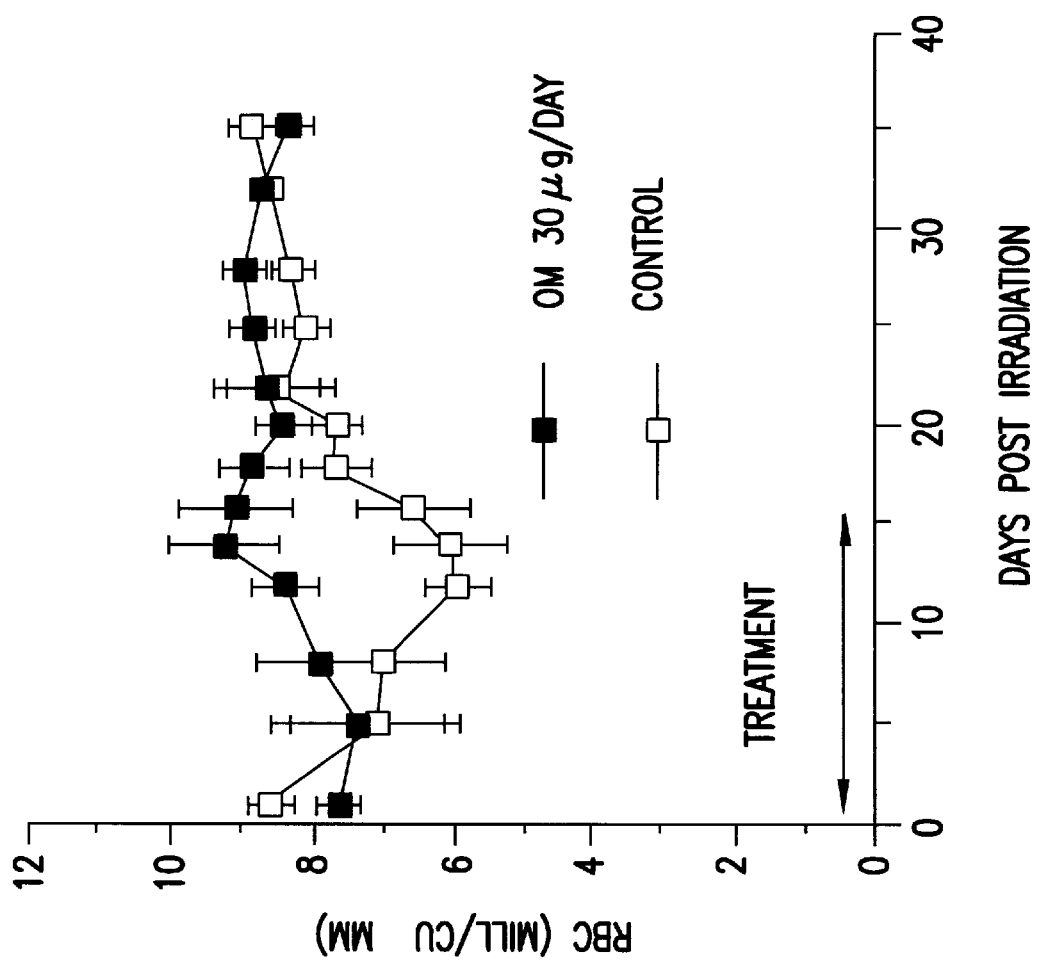

Another symptom of radiation therapy, particularly at higher dosages is anemia. In this set of experiments, mice were irradiated with 500 Rads of γ-irradiation and the mice were treated with 30 Ag/day OM for 15 days. Blood samples were taken from the orbital sinus and assayed for red blood cell counts (FIG. 7). In contrast to other thrombocytopoietic cytokines (e.g., IL-6, IL-11) which had been reported to induce and/or exacerbate anemia, animals treated with OM (in contrast to control) did not demonstrate a decrease in red blood cell counts following irradiation.

Figure 8:
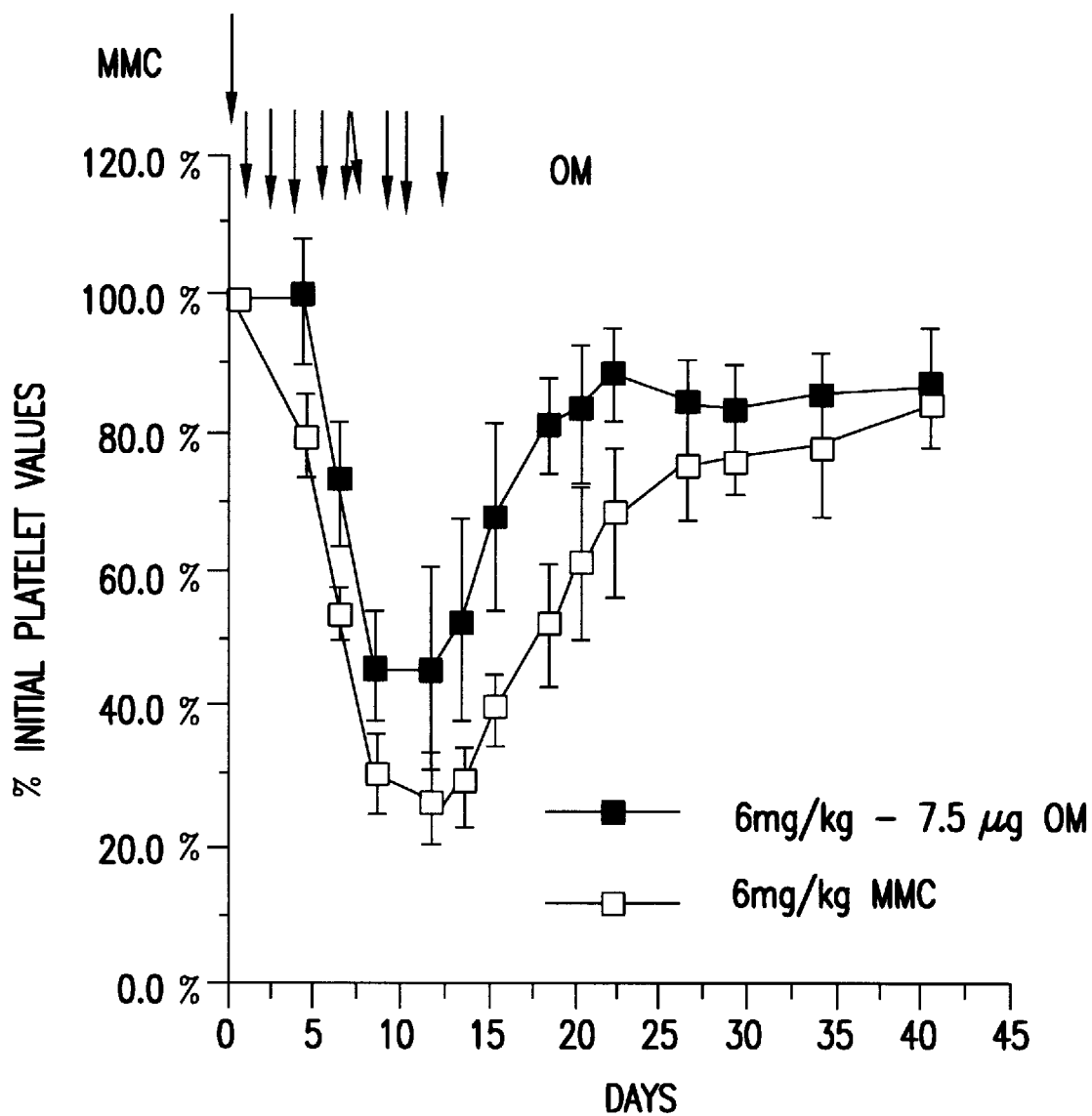

A murine model was also used to examine the effects of OM on chemotherapy-induced thrombocytopenia and on the anti-tumor activity of a cytotoxic agent. In the study of chemotherapy-induced thrombocytopenia, mice were treated with Mitomycin C (MMC) (6 mg/kg i.v.). One day following drug administration, treatment was initiated with twice daily injections (15 µg/day) of OM and continued for 11 days (three rounds of three-day treatment with one day rest between rounds). Blood samples were taken via the orbital sinus and platelet counts determined. The results are expressed as a percentage of initial platelet number (FIG. 8). As seen previously following irradiation, there was a reduction in the nadir of the platelets in OM-treated mice compared to animals not treated with OM, and the rate of recovery to normal platelet levels was accelerated when compared to controls.

Figure 9:
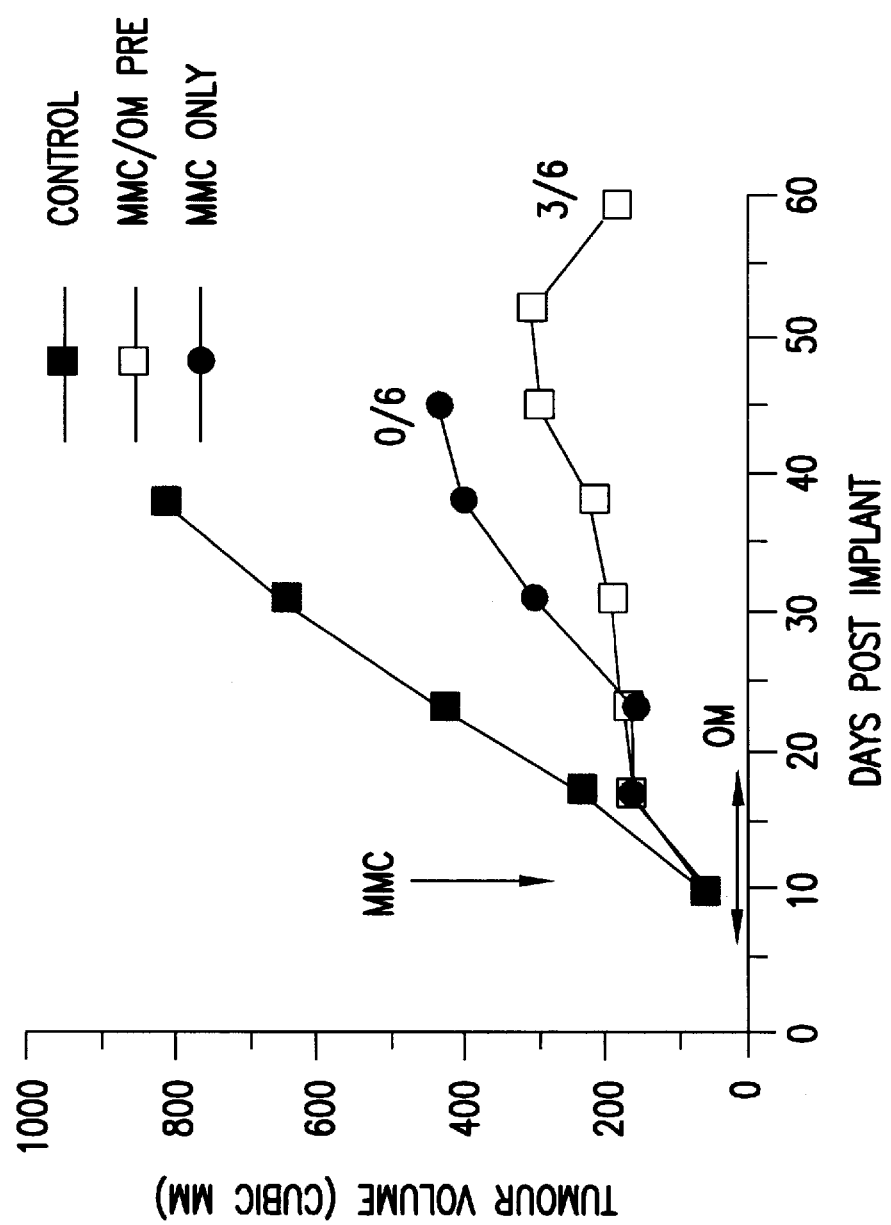

The effect of OM on the anti-tumor activity of MMC was also determined in the murine model. In this study, mice (seven mice/group) were implanted subcutaneously with a human melanoma cell line A375. Three days following the initiation of treatment with OM (15 µg/12h×20), or with diluent as controls, a single injection of MMC at its maximum tolerated dose was administered. As seen in FIG. 9, in this study, the combination of OM and MMC had greater tumor inhibitory effects than MMC alone. Three animals from the group of mice receiving the combination remained tumor-free 60 days following the implant.

Figure 10A:
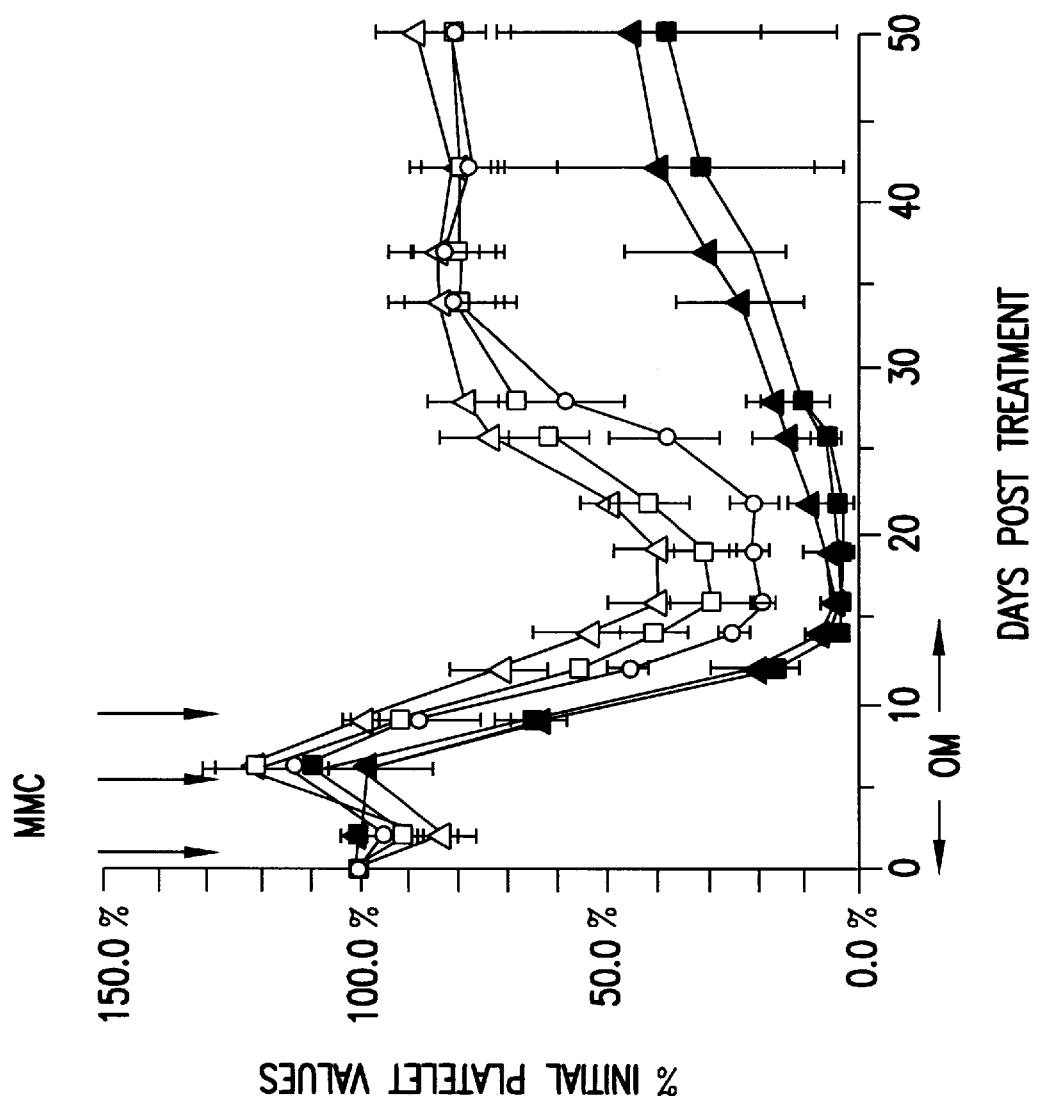
Figure 10B:
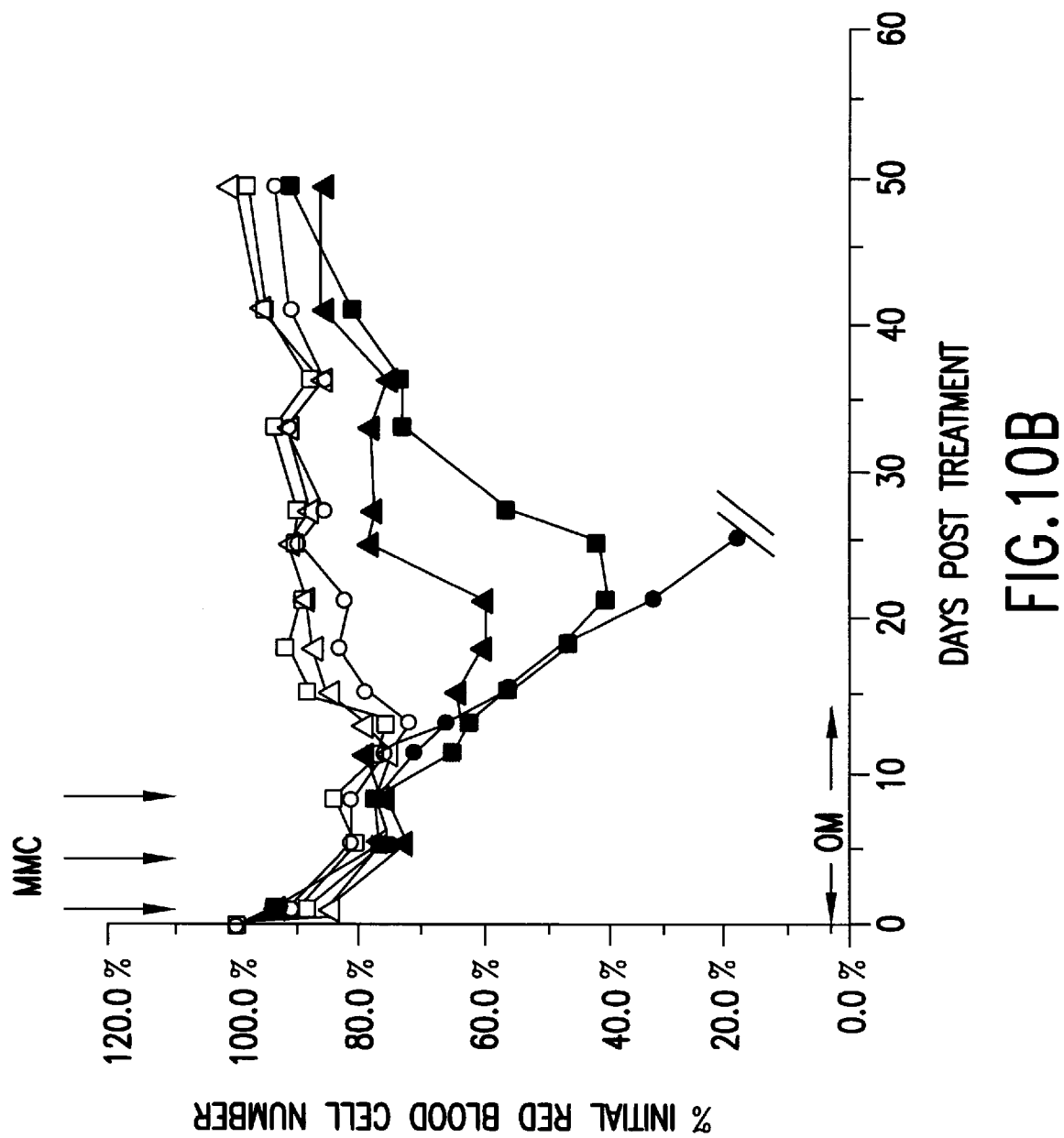

When MMC was given in a therapeutic regimen on days 1, 5 and 9, OM was not only capable of alleviating the thrombocytopenia, but increased the dose of MMC tolerated and reduced drug related anemia. At a dose of 7.5 µg of OM given i.v. twice daily for 15 days, OM reduced the severity of thrombocytopenia (FIG. 10A). At a higher dose of MMC (4 mg/kg), the survival of the animals was improved from 1 out of 5 in the control group to 4 out of 5 in both OM groups and the severity of anemia was reduced (FIG. 10B).

8. EXAMPLE: THROMBOCYTOPOIETIC ACTIVITY OF ONCOSTATIN M AS MEASURED IN A NORMAL NON-HUMAN PRIMATE MODEL

8.1. MATERIAL AND METHODS

8.1.1. ANIMALS AND REAGENTS

Male Macaca facicularis monkeys (4–6 kg) were obtained from Charles River Primates Corporation (Houston, Texas). OM formulated at 1 mg/ml in 40% acetonitrile+0.05% TFA and stored at −20° C. was used for this study. Each dose was prepared fresh by drying the appropriate quantity of stock solution with autologous monkey serum. At the time of use, the OM was reconstituted in approximately 600 µl of PBS+0.1% autologous monkey serum. Control monkeys received 40% acetonitrile+0.05% TFA dried down and reconstituted in a similar manner to the OM doses.

Blood samples were drawn at 10, 7 and 5 days prior to the beginning of the study. After initiation of the study, blood samples were taken every two or three days. Samples were analyzed for complete blood counts.

8.1.2. ADMINISTRATION OF ONCOSTATIN M

This study examined escalating doses of OM on platelet and red blood cell counts in normal non-human primates. Animals were treated with equal doses twice per day (approximately 8–10 hours apart) by subcutaneous injection for 7 or 3 days. Animals were retreated 4–6 weeks later as shown in Table 3.

TABLE 3

| | OM TREATMENT REGIMEN | | | |
|---|---|---|---|---|
| | First Treatment | | Second Treatment | |
| Monkey # | Daily Dose | # Days | Daily Dose | # Days |
| 58 | 10 µg/kg | 7 | 30 µg/kg | 3 |
| 97 | 30 µg/kg | 7 | 30 µg/kg | 3 |
| 43 | 90 µg/kg | 3 | 86 µg/kg | 3 |

8.2 RESULTS

Figure 11A:
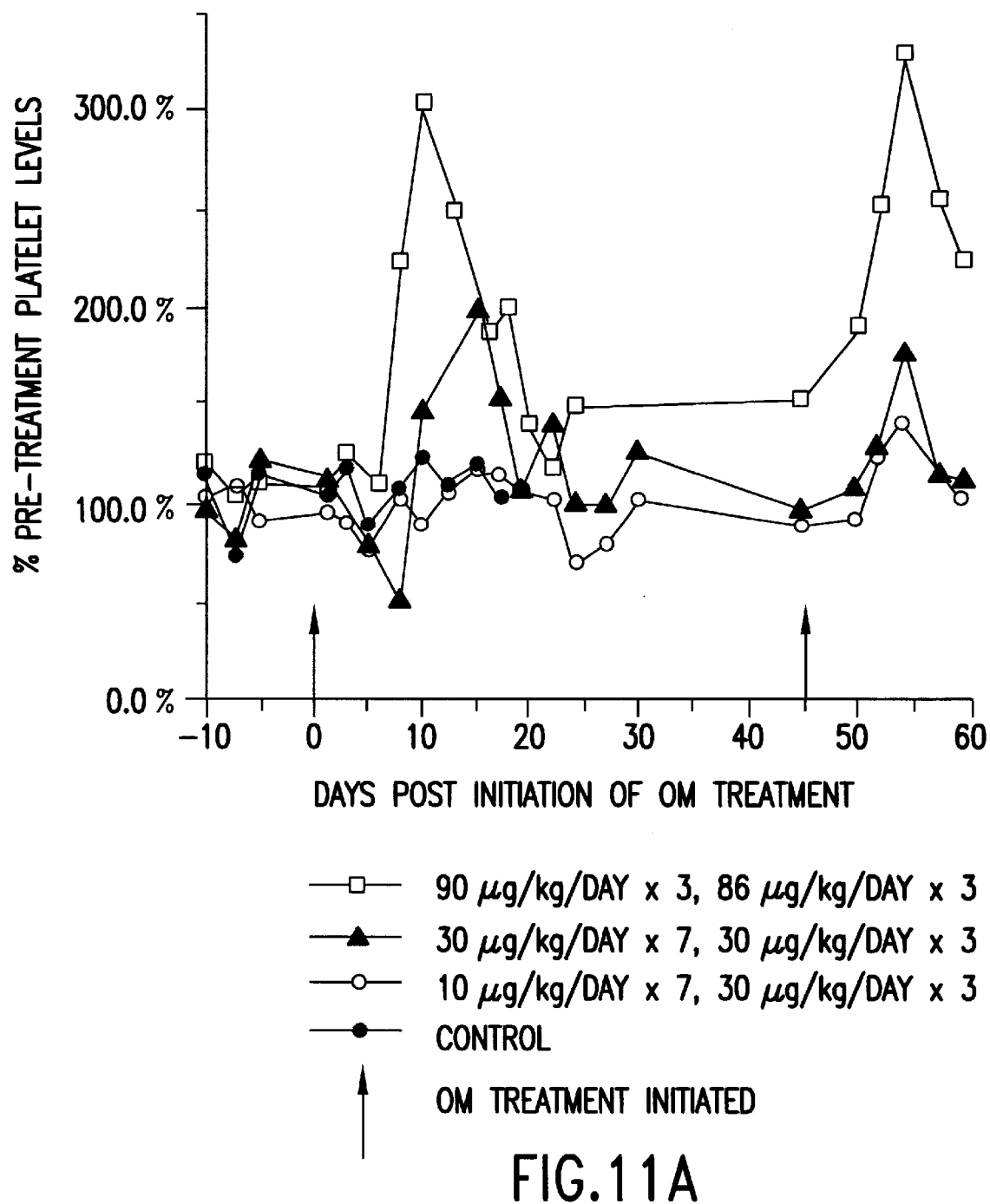
Figure 11B:
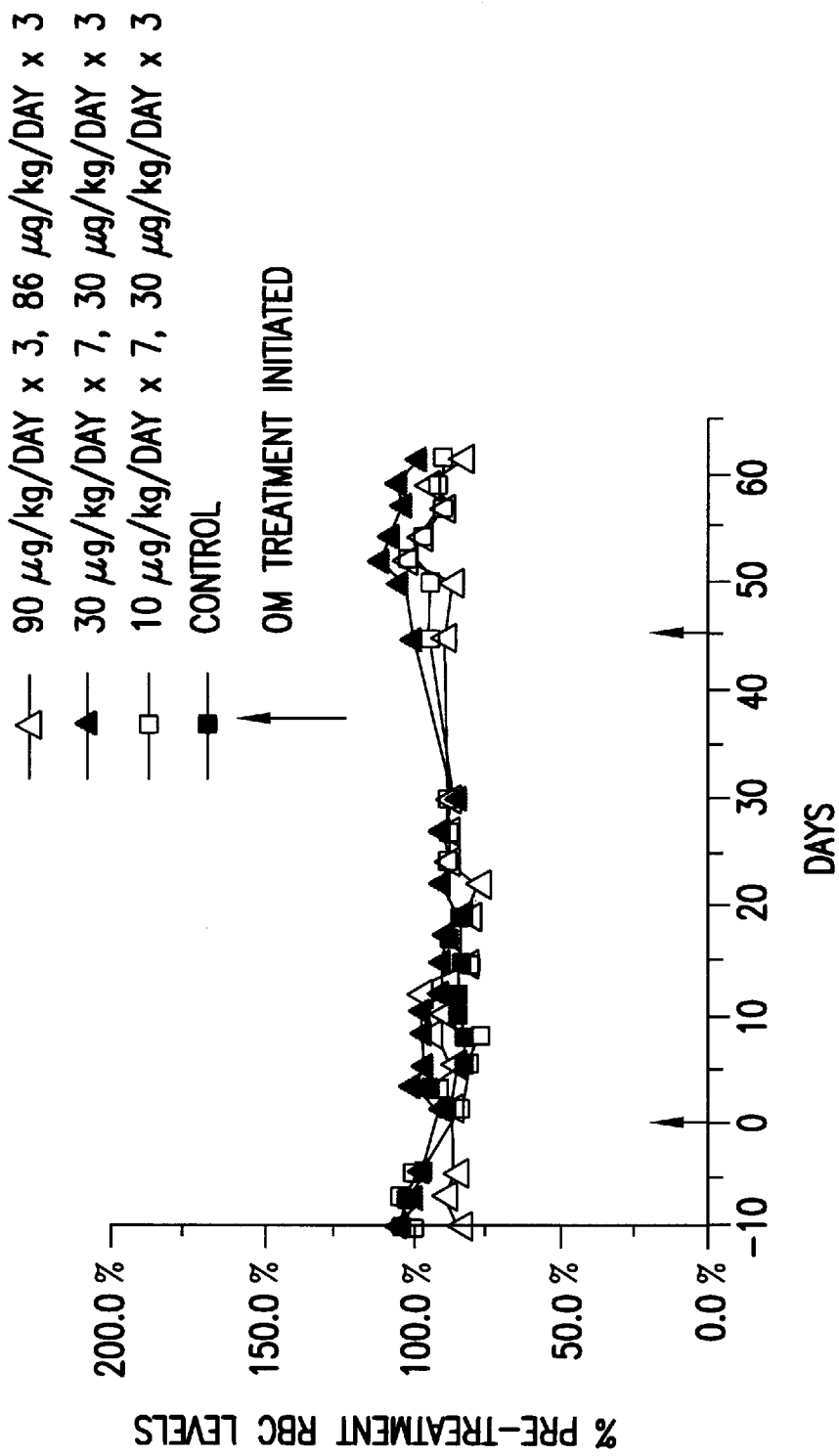

This study evaluated the effect of OM on the relative number of platelets and red blood cells in non-human primates with an escalating dose of OM. Subcutaneous injections of OM increased platelet counts in a dose dependent fashion (FIG. 11A). Platelets increased as high as 300% of pre-treatment levels in the highest dose animal (90 Ag/kg). There was no evidence of toxicity or decrease in RBC in any of the animals (FIG. 11B). There was no weight loss, no loss of appetite and no noticeable behavioral changes in any of the animals. The animal that received 30 Ag/kg first for 7 days and then for 3 days in the second treatment experienced an approximately 200% increase in platelets following each treatment (FIG. 11A). Treatment with 10 µg/kg for 7 days produced a modest increase in platelets. When this animal was further treated with 30 µg/kg OM for three days, platelet levels increased to 150% of pretreatment levels (FIG. 11A).

Figure 12:
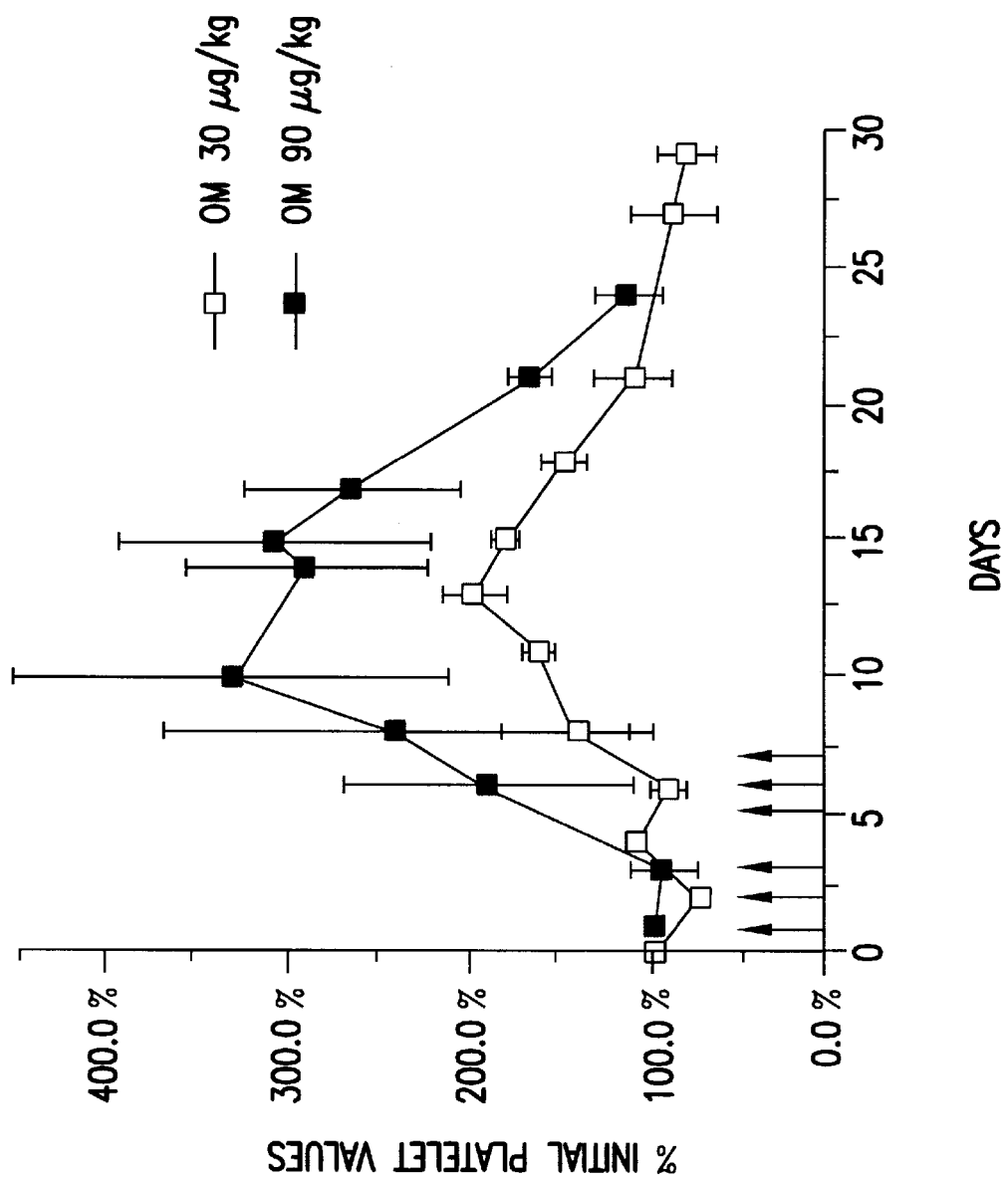

In a further study, female Rhesus monkeys (*Macaca mulatta*) were injected as in the previous study with 12, twice daily injections of OM over 7 days at 30 Ag/kg/day and 90 µg/kg/day. Platelet level increased in treated monkeys and several days after the completion of the OM treatment, the platelet levels reached a peak (approximately 180% of pretreatment levels at 30 µg/kg/day and greater than 300% at 90 µg/kg/day) subsequently dropping back to pretreatment levels after an additional 10 to 15 days (FIG. 12). Both dosage levels of OM appear to have been well tolerated.

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for regulating cell growth comprising contacting an individual's normal endothelial cells with an amount of Oncostatin M sufficient to induce the synthesis of IL-6 in an amount sufficient to regulate cell growth, wherein said regulated cell is not regulated by contact with Oncostatin M alone.

2. A method for regulating leukocyte differentiation comprising contacting an individual's normal endothelial cells with an amount of Oncostatin M sufficient to induce the synthesis of IL-6 in an amount sufficient to regulate leukocyte differentiation, wherein said differentiation of said leukocytes is not regulated by contact with Oncostatin M alone.

3. A method for inhibiting tumor cell growth comprising contacting an individual's normal endothelial cells with an amount of Oncostatin M sufficient to induce the synthesis of IL-6 in an amount sufficient to inhibit tumor cell growth, wherein said tumor cell is not sensitive to inhibition by Oncostatin M alone.

4. A method of any one of claims 1, 2 or 3 wherein said effective amount of Oncostatin M is in the range of about 0.01 mg/kg body weight to about 20 mg/kg body weight.

* * * * *